US011007372B2

(12) United States Patent
Lee et al.

(10) Patent No.: US 11,007,372 B2
(45) Date of Patent: May 18, 2021

(54) SELECTIVE ACTIVATION OF CORTEX USING BENT MICRO WIRES TO MAGNETICALLY STIMULATE NEURONS

(71) Applicant: The General Hospital Corporation, Boston, MA (US)

(72) Inventors: Seungwoo Lee, Boston, MA (US); Shelley Fried, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 145 days.

(21) Appl. No.: 16/086,584

(22) PCT Filed: Mar. 22, 2017

(86) PCT No.: PCT/US2017/023605
§ 371 (c)(1),
(2) Date: Sep. 19, 2018

(87) PCT Pub. No.: WO2017/165530
PCT Pub. Date: Sep. 28, 2017

(65) Prior Publication Data
US 2019/0099609 A1    Apr. 4, 2019

Related U.S. Application Data

(60) Provisional application No. 62/311,609, filed on Mar. 22, 2016.

(51) Int. Cl.
A61N 2/00    (2006.01)
A61N 2/02    (2006.01)
A61N 1/05    (2006.01)

(52) U.S. Cl.
CPC ............... A61N 2/006 (2013.01); A61N 2/02 (2013.01); A61N 1/0534 (2013.01)

(58) Field of Classification Search
CPC ......... A61N 2/02; A61N 2/006; A61N 1/0534
(Continued)

(56) References Cited

U.S. PATENT DOCUMENTS

2006/0276866 A1*  12/2006  McCreery ............ A61N 1/0534
                                                              607/116
2008/0046055 A1*   2/2008  Durand ................ A61N 1/0556
                                                              607/118

(Continued)

OTHER PUBLICATIONS

Current distribution in circular planar coil, Engineering Analysis with Boundary, Papagiannopoulos, G. De Mey, V. Chatziathanasiou, Elements.vol. 37, Issue 4, Apr. 2013, pp. 747-756 (Year: 2013).*

(Continued)

Primary Examiner — Navin Natnithithadha
Assistant Examiner — Sunita Reddy
(74) Attorney, Agent, or Firm — Quarles & Brady LLP

(57) ABSTRACT

Disclosed are micro-wire stimulators that magnetically stimulate nearby cells and/or their processes (e.g., nerve fiber, axons, dendrites, etc.). The micro-wire includes one or more bends. The micro-wire stimulator can facilitate the creation of stronger field gradients in one direction with much smaller gradients in orthogonal directions, allowing for selective targeting, or avoiding, of specific cell types within a targeted region. The bent micro-wire stimulator may be implanted into the cortex of the brain to selectively stimulate nearby neural cells having a particular orientation relative to the stimulator. A tip portion of the micro-wire may be rounded, or it may have corners forming other suitable geometric shapes.

20 Claims, 17 Drawing Sheets

(58) Field of Classification Search
USPC ...................................................... 600/9–15
See application file for complete search history.

(56) References Cited

U.S. PATENT DOCUMENTS

| | | | | |
|---|---|---|---|---|
| 2009/0198293 | A1* | 8/2009 | Cauller | A61B 5/0031 607/2 |
| 2009/0254146 | A1* | 10/2009 | Bonmassar | A61N 2/004 607/45 |
| 2013/0331905 | A1* | 12/2013 | Haessler | A61N 1/0514 607/41 |
| 2014/0163644 | A1* | 6/2014 | Scott | A61N 1/36139 607/60 |
| 2014/0243714 | A1* | 8/2014 | Ward | A61B 5/04 601/2 |
| 2014/0275718 | A1* | 9/2014 | Huang | A61N 2/006 600/12 |
| 2014/0275719 | A1* | 9/2014 | Gale | A61N 2/006 600/14 |
| 2014/0357933 | A1* | 12/2014 | Lee | A61N 2/02 600/12 |
| 2015/0080637 | A1* | 3/2015 | Bonmassar | A61N 2/006 600/14 |
| 2015/0157385 | A1* | 6/2015 | Schwagten | A61B 18/10 606/31 |
| 2015/0290457 | A1* | 10/2015 | Palermo | A61N 1/0452 607/67 |
| 2015/0328477 | A1* | 11/2015 | Gale | A61N 2/02 600/13 |
| 2016/0074671 | A1* | 3/2016 | Burnett | A61N 1/36007 600/13 |
| 2016/0129276 | A1* | 5/2016 | Fried | A61N 2/006 600/12 |
| 2016/0213943 | A1 | 7/2016 | Mauger et al. | |

OTHER PUBLICATIONS

Barrese et al., Failure Mode Analysis of Silicon-Based Intracortical Microelectrode Arrays in Non-Human Primates, Journal of Neural Engineering, 2013, 10(6):066014, 47 pages.
Behrend et al., Selective Labeling of Retinal Ganglion Cells with Calcium Indicators by Retrograde Loading In Vitro, Journal of Neuroscience Methods, 2009, 179(2):166-172.
Bonmassar et al., Microscopic Magnetic Stimulation of Neural Tissue, Nature Communications, 2012, 3(1):1-10.
Born et al., Segregation of Object and Background Motion in Visual Area MT: Effects of Microstimulation on Eye Movements, Neuron, 2000, 26(3):725-734.
Bradley et al., Visuotopic Mapping Through a Multichannel Stimulating Implant in Primate V1, Journal of Neurophysiology, 2005, 93(3):1659-1670.
Brecht et al., Organization of Rat Vibrissa Motor Cortex and Adjacent Areas According to Cytoarchitectonics, Microstimulation, and Intracellular Stimulation of Identified Cells, Journal of Comparative Neurology, 2004, 479(4):360-373.
Brecht et al., Whisker Movements Evoked by Stimulation of Single Pyramidal Cells in Rat Motor Cortex, Nature, 2004, 427(6976):704-710.
Chung et al., Structural and Molecular Interrogation of Intact Biological Systems, Nature, 2013, 497(7449):332-337.
Davis et al., Spatial and Temporal Characteristics of V1 Microstimulation During Chronic Implantation of a Microelectrode Array in a Behaving Macaque, Journal of Neural Engineering, 2012, 9(6):065003, 23 pages.
DeYoe et al., Laminar Variation in Threshold for Detection of Electrical Excitation of Striate Cortex by Macaques, Journal of Neurophysiology, 2005, 94(5):3443-3450.
Felleman et al., Distributed Hierarchical Processing in the Primate Cerebral Cortex, Cerebral Cortex, 1991, 1(1):1-47.

Fried et al., Axonal Sodium-Channel Bands Shape the Response to Electric Stimulation in Retinal Ganglion Cells, Journal of Neurophysiology, 2009, 101(4):1972-1987.
Fries, Cortical Projections to the Superior Colliculus in the Macaque Monkey: A Retrograde Study Using Horseradish Peroxidase, Journal of Comparative Neurology, 1984, 230(1):55-76.
Ghose et al., A Strong Constraint to the Joint Processing of Pairs of Cortical Signals, Journal of Neuroscience, 2012, 32(45):15922-15933.
Grill et al., Implanted Neural Interfaces: Biochallenges and Engineered Solutions, Annual Review of Biomedical Engineering, 2009, 11:1-24.
Grumet et al., Multi-Electrode Stimulation and Recording in the Isolated Retina, Journal of Neuroscience Methods, 2000, 101(1):31-42.
Heffner et al., Sound Localization in Chinchillas. I: Left/Right Discriminations, Hearing Research, 1994, 80(2):247-257.
Histed et al., Direct Activation of Sparse, Distributed Populations of Cortical Neurons by Electrical Microstimulation, Neuron, 2009, 63(4):508-522.
Histed et al., Insights into Cortical Mechanisms of Behavior from Microstimulation Experiments, Progress in Neurobiology, 2013, 103:115-130.
Im et al., Indirect Activation Elicits Strong Correlations Between Light and Electrical Responses in ON but not Off Retinal Ganglion Cells, The Journal of Physiology, 2015, 593(16):3577-3596.
Jensen et al., Activation of Retinal Ganglion Cells in Wild-Type and rd1 Mice Through Electrical Stimulation of the Retinal Neural Network, Vision Research, 2008, 48(14):1562-1568.
Karumbaiah et al., Relationship Between Intracortical Electrode Design and Chronic Recording Function, Biomaterials, 2013, 34(33):8061-8074.
Kelly et al., Behavioral Limits of Auditory Temporal Resolution in the Rat: Amplitude Modulation and Duration Discrimination, Journal of Comparative Psychology, 2006, 120(2):98-105.
Koivuniemi et al., Asymmetric Versus Symmetric Pulses for Cortical Microstimulation. IEEE Transactions on Neural Systems and Rehabilitation Engineering, 2011, 19(5):468-476.
Koivuniemi et al., Multimodal, Longitudinal Assessment of Intracortical Microstimulation, Progress in Brain Research, 2011, vol. 194, pp. 131-144.
Johnson et al., Repeated Voltage Biasing Improves Unit Recordings by Reducing Resistive Tissue Impedances, IEEE Transactions on Neural Systems and Rehabilitation Engineering, 2005, 13(2):160-165.
Lee et al., Responses to Pulsatile Subretinal Electric Stimulation: Effects of Amplitude and Duration, Journal of Neurophysiology, 2013, 109(7):1954-1968.
Lee et al. The Response of L5 Pyramidal Neurons of the PFC to Magnetic Stimulation from a Micro-Coil, In 2014 36th Annual International Conference of the IEEE Engineering in Medicine and Biology Society, 2014, pp. 6125-6128.
Lee et al., Suppression of Subthalamic Nucleus Activity by Micromagnetic Stimulation, IEEE Transactions on Neural Systems and Rehabilitation Engineering, 2015, 23(1):116-127.
Martin et al., Form, Function and Intracortical Projections of Spiny Neurones in the Striate Visual Cortex of the Cat, Journal of Physiology, 1984, 353(1):463-504.
Matyas et al., Motor Control by Sensory Cortex, Science, 2010, 330(6008):1240-1243.
McIntyre et al., Selective Microstimulation of Central Nervous System Neurons, Annals of Biomedical Engineering, 2000, 28(3):219-233.
McIntyre et al., Extracellular Stimulation of Central Neurons: Influence of Stimulus Waveform and Frequency on Neuronal Output, Journal of Neurophysiology, 2002, 88(4):1592-1604.
Merrill et al., Impedance Characterization of Microarray Recording Electrodes In Vitro, Proceedings of the 26th Annual International Conference of the IEEE Engineering in Medicine and Biology Society, 2004, vol. 6, pp. 4349-4352.
Molnar et al., Towards the Classification of Subpopulations of Layer V Pyramidal Projection Neurons, Neuroscience Research, 2006, 55(2):105-115.

(56) References Cited

OTHER PUBLICATIONS

Nassi et al., Parallel Processing Strategies of the Primate Visual System, Nature Reviews Neuroscience, 2009, 10(5):360-372.
Nassi et al., Corticocortical Feedback Contributes to Surround Suppression in V1 of the Alert Primate, Journal of Neuroscience, 2013, 33(19):8504-8517.
Ni et al., Microstimulation Reveals Limits in Detecting Different Signals from a Local Cortical Region, Current Biology, 2010, 20(9):824-828.
Otto et al., Voltage Pulses Change Neural Interface Properties and Improve Unit Recordings with Chronically Implanted Microelectrodes, IEEE Transactions on Biomedical Engineering, 2006, 53(2):333-340.
Pack et al., Temporal Dynamics of a Neural Solution to the Aperture Problem in Visual Area MT of Macaque Brain, Nature, 2001, 409(6823):1040-1042.
Park et al., Activation of the Central Nervous System Induced by Micro-Magnetic Stimulation, Nature Communications, 2013, 4(1):1-9.
Ponce et al., Integrating Motion and Depth Via Parallel Pathways, Nature Neuroscience, 2008, 11(2):216-223.
Prasad et al., Comprehensive Characterization and Failure Modes of Tungsten Microwire Arrays in Chronic Neural Implants, Journal of Neural Engineering, 2012, 9(5):056015, 21 pages.
Price et al., Timescales of Sensory- and Decision-Related Activity in the Middle Temporal and Medial Superior Temporal Areas, Journal of Neuroscience, 2010, 30(42):14036-14045.
Ranck Jr, Which Elements are Excited in Electrical Stimulation of Mammalian Central Nervous System: A Review, Brain Research, 1975, 98(3):417-440.
Rattay, The Basic Mechanism for the Electrical Stimulation of the Nervous System, Neuroscience, 1999, 89(2):335-346.
Schmidt et al., Feasibility of a Visual Prosthesis for the Blind Based on Intracortical Micro Stimulation of the Visual Cortex, Brain, 1996, 119(2):507-522.
Sincich et al., The Circuitry of V1 and V2: Integration of Color, Form, and Motion, Annu. Rev. Neurosci., 2005, 28:303-326.
Smolyanskaya et al., A Modality-Specific Feedforward Component of Choice-Related Activity in MT, Neuron, 2015, 87(1):208-219.
Sparks, Conceptual Issues Related to the Role of the Superior Colliculus in the Control of Gaze, Current Opinion in Neurobiology, 1999, 9(6):698-707.
Tehovnik et al., Saccadic Eye Movements Evoked by Microstimulation of Striate Cortex, European Journal of Neuroscience, 2003, 17(4):870-878.
Tehovnik et al., Direct and Indirect Activation of Cortical Neurons by Electrical Microstimulation, Journal of Neurophysiology, 2006, 96(2):512-521.
Tehovnik et al., Depth-Dependent Detection of Microampere Currents Delivered to Monkey V1, European Journal of Neuroscience, 2009, 29(7):1477-1489.
Watson et al., QUEST: A Bayesian Adaptive Psychometric Method, Perception & Psychophysics, 1983, 33(2):113-120.
Wei et al., Impedance Characteristics of Deep Brain Stimulation Electrodes In Vitro and In Vivo, Journal of Neural Engineering, 2009, 6(4):046008, 9 pages.
Williams et al., Complex Impedance Spectroscopy for Monitoring Tissue Responses to Inserted Neural Implants, Journal of Neural Engineering, 2007, 4(4):410-423.
Wilks et al., Poly (3, 4-ethylene dioxythiophene)(PEDOT) as a Micro-Neural Interface Material for Electrostimulation, Frontiers in Neuroengineering, 2009, vol. 2, Article 7, 8 pages.
PCT International Search Report and Written Opinion, PCT/US2017/023605, dated Jun. 20, 2017, 12 pages.

\* cited by examiner

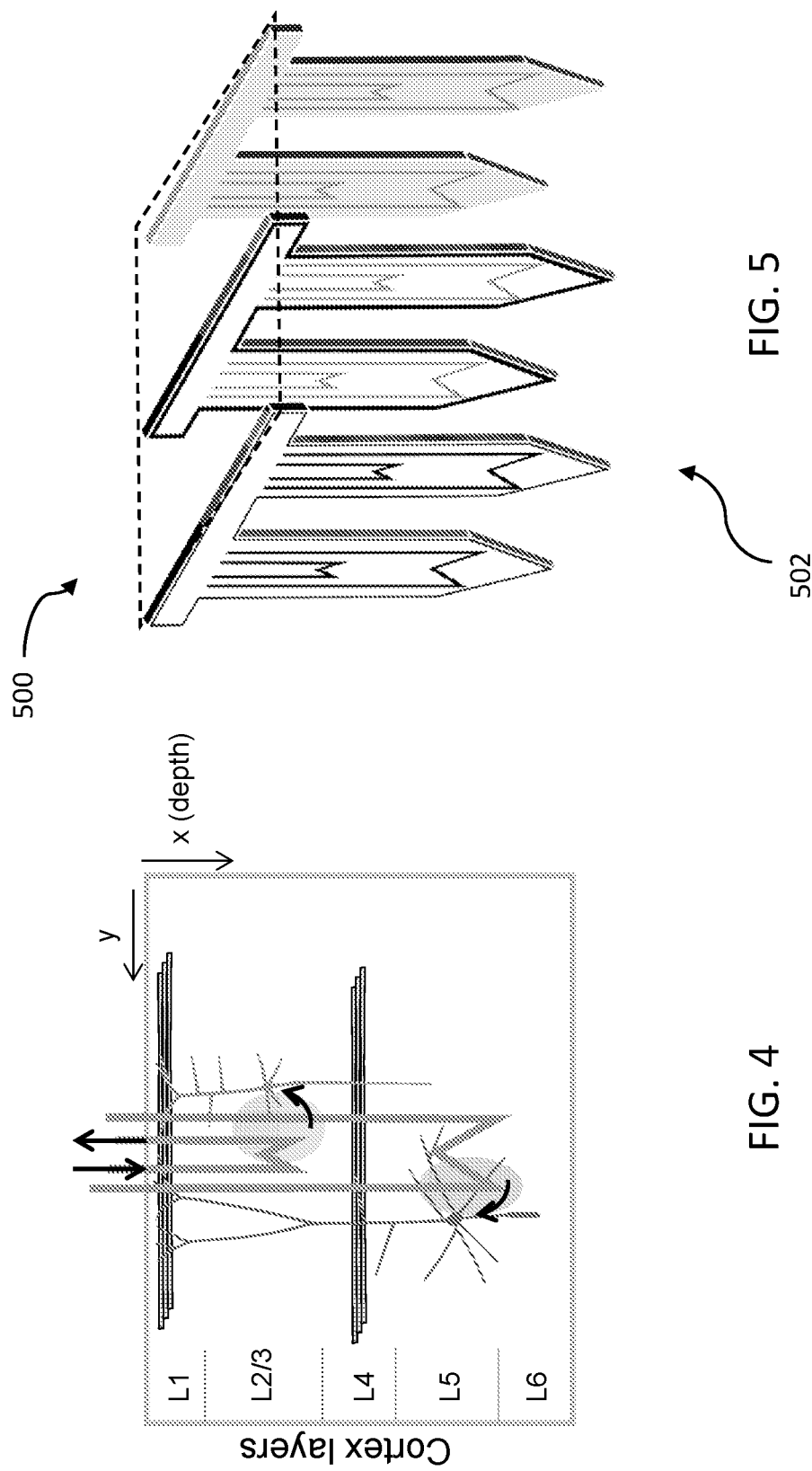

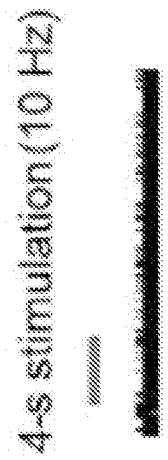
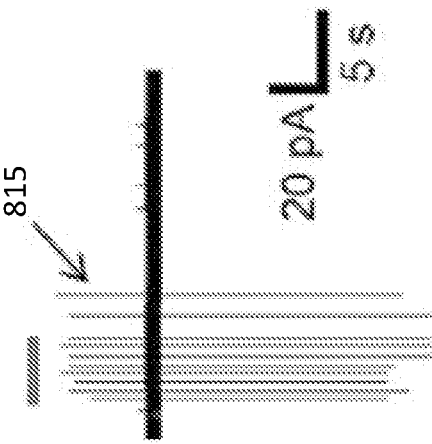
FIG. 8B
FIG. 8D
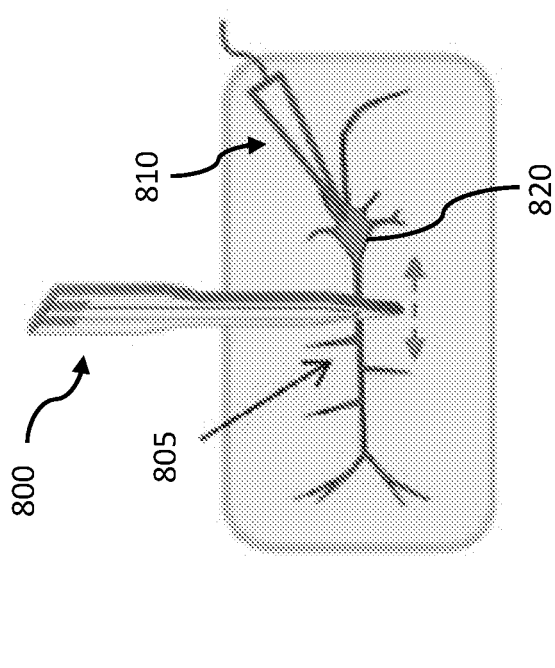
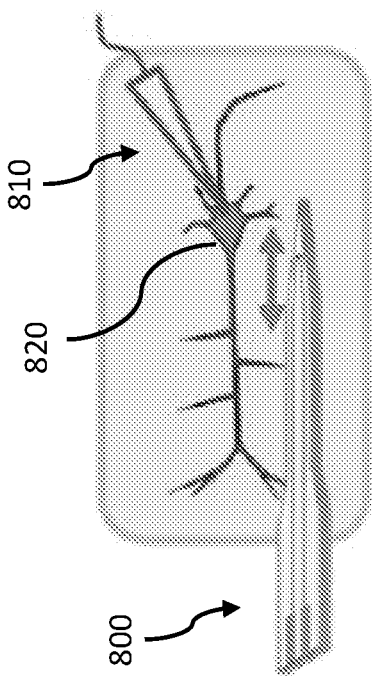
FIG. 8A
FIG. 8C

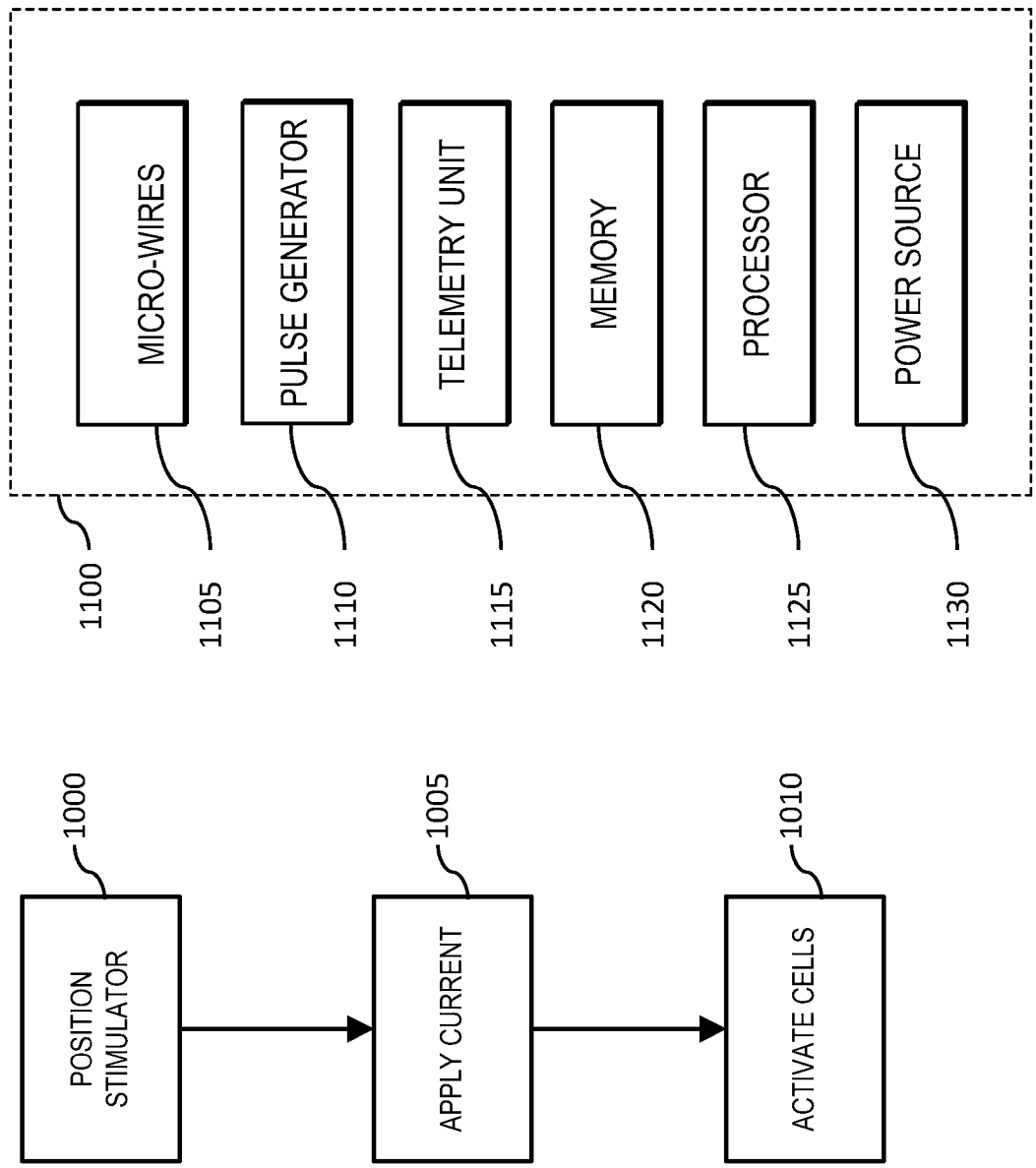

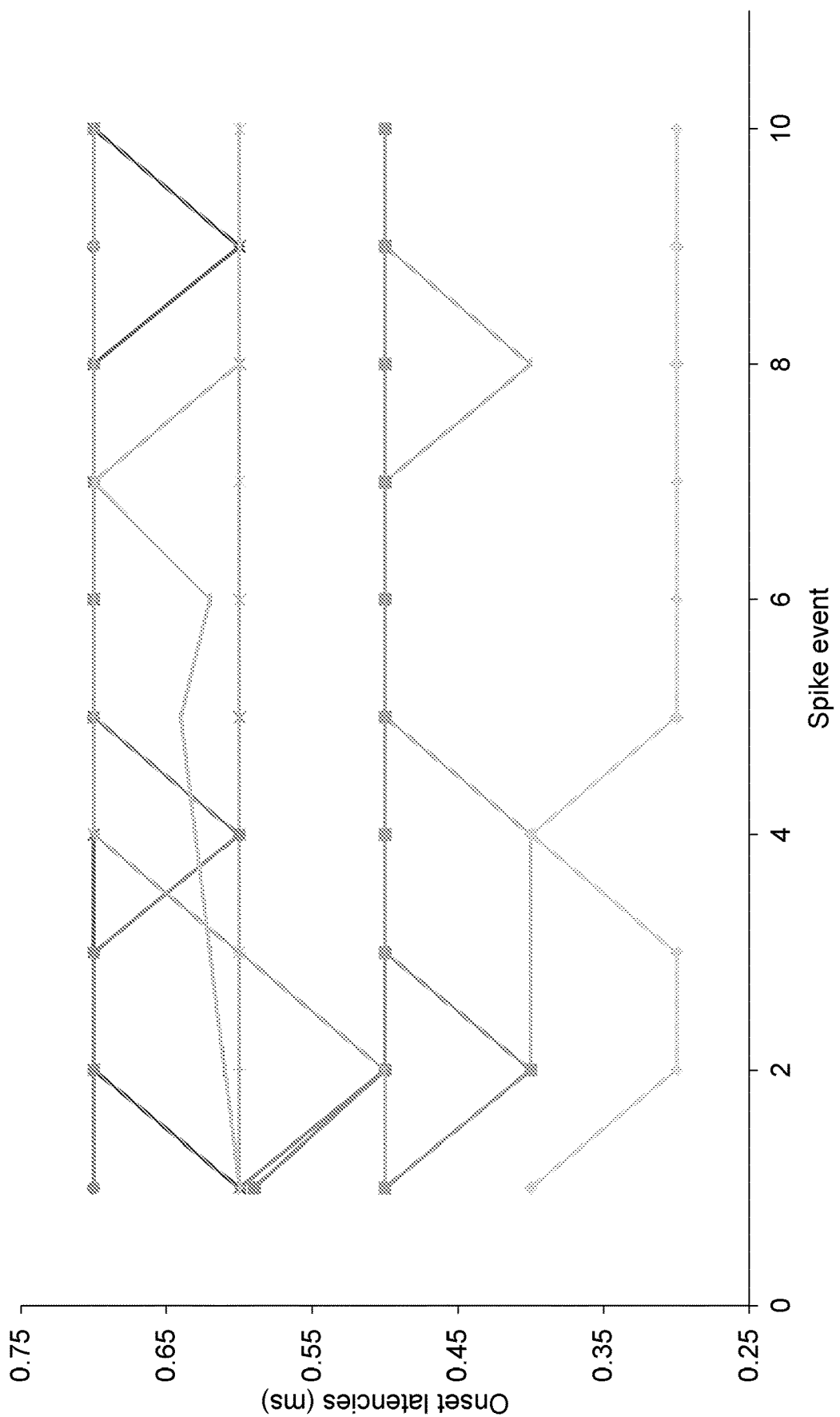

SELECTIVE ACTIVATION OF CORTEX USING BENT MICRO WIRES TO MAGNETICALLY STIMULATE NEURONS

CROSS REFERENCE TO RELATED APPLICATIONS

This application is a U.S. National Stage of PCT Application No. PCT/US2017/023605 filed on Mar. 22, 2017 which is based on, claims priority to, and incorporates herein by reference in its entirety U.S. Provisional Application Ser. No. 62/311,609, filed Mar. 22, 2016, and entitled, "Microcoil Implants for Selective Activation of Cortical Neurons." The references cited in the above provisional patent application are also hereby incorporated by reference.

STATEMENT REGARDING FEDERALLY SPONSORED RESEARCH

This invention was made with government support under NIH/NEI R01 EY023651 and NIH/NINDS U01 NS099700 awarded by the National Institutes of Health and VA/RR&D RX001663 awarded by the Department of Veterans Affairs. The government has certain rights in the invention.

BACKGROUND

The ability of electrical stimulation delivered from small micro-electrodes to modulate the activity of CNS neurons has opened up the possibility that implant arrays can be used to treat a wide range of neurological disorders. Notable successes include implantation of arrays of electrodes into the cochlea (cochlear prosthesis) to restore hearing to the profoundly deaf, and implantation of a single probe containing four distinct electrodes into the sub-thalamic nucleus, or other targets within the basal ganglia, to treat Parkinson's Disease or other disorders of the motor system. These successes have inspired much new effort over the last few decades to implant electrodes into many other regions of the central nervous system (CNS), including the neocortex, with the hope of treating many additional disorders. For example, arrays of microelectrodes have been implanted into the primary visual cortex with the goal of restoring vision to blind subjects. Encouragingly, subjects consistently report light percepts (phosphenes) in response to stimulation from a single electrode, and stimulation from an adjacent electrode elicits a phosphene in an adjacent region of visual space. Much additional effort has been devoted to stimulation of somatosensory cortex to provide somatosensory and proprioceptive feedback, e.g. as part of a brain-computer interface (BCI) in which cortical signals are "read" by the interface to allow the user to gain control of a prosthetic arm; the feedback signal is used to provide relevant feedback to the user, such as the force being exerted to grip a cup that is being lifted by the prosthetic arm. In addition to prosthetic-based applications, precise stimulation of the cortex has been and continues to be an essential component of many research studies that study fundamental questions of brain anatomy and/or physiology.

Unfortunately, the long-term viability of implantable cortical electrodes has been limited by the biological reactions that arise in response to implantation as well as by the fundamental biophysics of electric stimulation. For example, prolonged implantation alters the properties of the electrode, especially at the junction between the exposed metal and the surrounding insulation. Functionally, this changes the impedance of the electrode and thus the effectiveness with which stimulation is delivered. Another significant concern arises from the complex biological reactions induced by the implantation of any foreign material into cortex; activated astrocytes can encapsulate individual electrodes, forming a high-impedance barrier that can diminish the effectiveness of stimulation. It is likely that these types of changes contribute to reported difficulties in maintaining response consistency over time with implanted electrodes. For example, electrodes implanted into the primary visual cortex (V1) of macaque monkeys each reliably elicited a visual percept (phosphene) shortly after implantation, but individual electrodes lost effectiveness within a few months. Although larger groupings of electrodes could be used to generate phosphenes (e.g. 2×2 or 3×3), the need to couple electrodes together represents a significant loss in potential visual acuity. The use of non-penetrating approaches, such as electrodes positioned on the surface of the cortex, has been proposed to alleviate some of these concerns but unfortunately, surface stimulation requires considerably higher levels of current to induce an effect and further, cannot produce the same level of focal activation as implants, thereby greatly limiting their effectiveness.

Another important limitation associated with the implantation of electrodes into cortex is that the electric field induced by stimulation is spatially symmetric. The driving force for activation of a neuron subjected to artificial stimulation is proportional to either the strength of the electric field induced by the stimulating electrode along its length or to the gradient of the induced field, i.e. a rapidly changing field along the length of an axon is highly effective in many situations. Referring to FIG. 1A, a spatially symmetric field 10 creates equal driving forces in all directions. As illustrated, the activating force for those neurons (or axons) oriented primarily along the x-axis 15 is approximately equal to the activating force for those neurons (or axons) oriented primarily along y-axis 20. Consequently, all nearby neuronal targets are activated regardless of their orientation relative to an electrode 25 that is inserted past skull 55, dura 50, and brain surface 30 and into cortex, which includes a target neuron 35 with its long axis aligned with the x-axis. This is especially problematic because the passing axons 40 that arise from distal neurons have their (orthogonal) long axes aligned with the y-axis and are highly sensitive to stimulation and their activation can lead to a wide range of undesirable side effects as well as to the spread of activation well beyond the local region surrounding a given electrode, thus diminishing the ability to create precise patterns of neural activity. Spatially symmetric fields also lead to the activation of both local excitatory neurons (mostly pyramidal neurons that project the results of local computations to other regions of the brain) as well as local inhibitory neurons (a heterogeneous group of neurons that provide feedback and limit the output of pyramidal neurons); the activation of local inhibitory neurons can negate the effect of stimulating nearby excitatory neurons.

Magnetic stimulation is an attractive alternative to electrical stimulation from implanted electrodes. This is because direct contact between the metal coils and the targeted neural tissue is not necessary and thus the stability of the interface is much less likely to deteriorate over time. Further, because magnetic fields pass readily through biological materials, they are not significantly diminished by even the most severe encapsulation, further enhancing the stability of coil performance over time. Note that while magnetic fields are not thought to directly modulate neuronal activity, the electric fields they induce are effective; thus, the electric field induced by the coil can be 'carried' beyond the region of encapsulation to drive activation. Coils small enough to be safely implanted into cortex were not thought to be sufficiently powerful to induce neural activation but recent studies have shown that small-sized inductors (coils) (0.5 mm width×1.0 mm length) could indeed modulate neuronal activity. While attractive, their size was still too large to safely implant into cortex, especially if such coils were to be part of a multi-coil array used to simultaneously modulate activity in multiple nearby regions. This is especially problematic because the orientation of the coil that best activates vertically-oriented pyramidal neurons necessitates the coil to be oriented in the horizontal direction, thereby increasing the cross-sectional area of the implant. Thus, it would be desirable to have a magnetic stimulator that is small enough to be safely implanted into cortex but still effective at providing selective stimulation and maintaining consistency over time.

SUMMARY OF THE PRESENT DISCLOSURE

Disclosed are exemplary systems and methods involving micro-wire stimulators capable of magnetically stimulating nearby cells. The design utilizes one or more bends in the micro-wire to enhance the strength of the induced field. In addition, precise arrangements of the bends can facilitate the creation of stronger field gradients in one direction with much smaller gradients in orthogonal directions, thus allowing for selective targeting, or avoiding, of specific cell types within a targeted region. In exemplary versions, a micro-wire stimulator may be implanted into the cortex of the brain to selectively stimulate nearby neural cells having a particular orientation relative to the stimulator. The micro-wire design results in a reduced cross-sectional surface area of the micro-wire stimulator; the smaller area helps to minimize both the trauma arising from implantation as well as the level of biological response that arises over time. Further advantages and features of the invention will be apparent from the remainder of this document in conjunction with the associated drawings.

BRIEF DESCRIPTION OF THE DRAWINGS

FIG. 4 depicts an exemplary pair of micro-wires having different lengths well-suited to targeting of different layers in the cortex, with arrows depicting electric current in the micro-wires.

FIG. 5 depicts an exemplary multi-wire microprobe array.

FIG. 8A is a schematic of an exemplary experimental setup in which a micro-wire assembly is positioned over the apical dendrites in a perpendicular orientation.

FIG. 8B depicts typical responses to the apical dendrite stimulation shown in FIG. 8A. The short horizontal bar indicates the duration over which stimulation was applied.

FIG. 8C is a schematic of an exemplary experimental setup in which a micro-wire assembly is positioned over the apical dendrites in a parallel orientation.

FIG. 8D depicts typical responses to the apical dendrite stimulation shown in FIG. 8C. The short horizontal bar indicates the duration over which stimulation was applied.

FIG. 10 is an exemplary process involving the positioning of a micro-wire stimulator for cellular activation.

FIG. 11 depicts components of an exemplary microprobe system for applying cellular stimulation.

FIG. 14D depicts typical latencies of action potentials to the proximal axonal stimulation shown in FIG. 14A in a parallel orientation.

The foregoing and other aspects and advantages of the invention will appear from the following description. In the description, reference is made to the accompanying drawings that form a part hereof, and in which there is shown by way of illustration preferred versions of the invention. Such versions do not necessarily represent the full scope of the invention, however, and reference is made therefore to the claims and herein for interpreting the scope of the invention. It is noted that components shown in the figures are not necessarily to scale.

DETAILED DESCRIPTION OF THE PRESENT DISCLOSURE

Figures 1A, 1B:
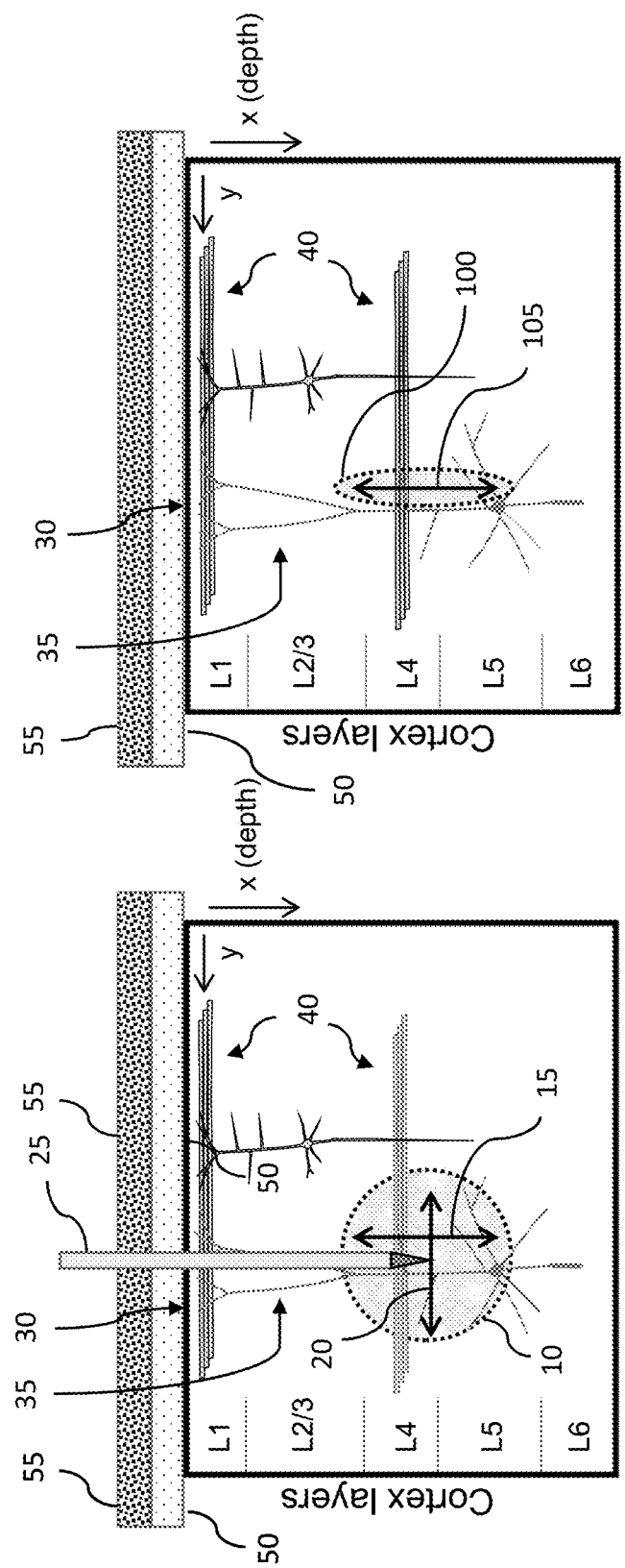
FIG. 1A depicts the use of an electrode to stimulate neurons, and the symmetric fields generated by the electrode.
FIG. 1B depicts spatially asymmetric fields with directional excitation well-suited to selective activation.

Magnetic stimulation offers several potential advantages over conventional electrode-based stimulation. For example, referring to FIG. 1B, unlike the fields arising from electrodes, the electric fields 100 that arise from magnetic stimulation from a bent micro-wire are spatially asymmetric and can therefore be harnessed to selectively activate some neuronal subpopulations while simultaneously avoiding others. As shown, excitation 105 is primarily in the x-axis (with much less y-axis excitation). In the cortex (below brain surface 30), this could include, for example, the ability to activate one or more vertically oriented pyramidal neurons (PNs) 35 without activating horizontally oriented passing axons 40. Another advantage of magnetic stimulation is that unlike the electric fields initiated by electrodes, magnetic fields pass readily through biological materials, and therefore their efficacy will not be diminished, even by severe encapsulation. A third advantage is that the lack of direct contact between the micro-wire and neural tissue makes this approach less prone to the numerous problems that can arise at the brain-electrode interface, such as damage to the electrode and/or the surrounding tissue that can arise from delivery of high levels of charge. Further, magnetic stimulators can be completely insulated with soft biocompatible materials that have been shown to mitigate the cortical response to implantation.

Figure 2A:
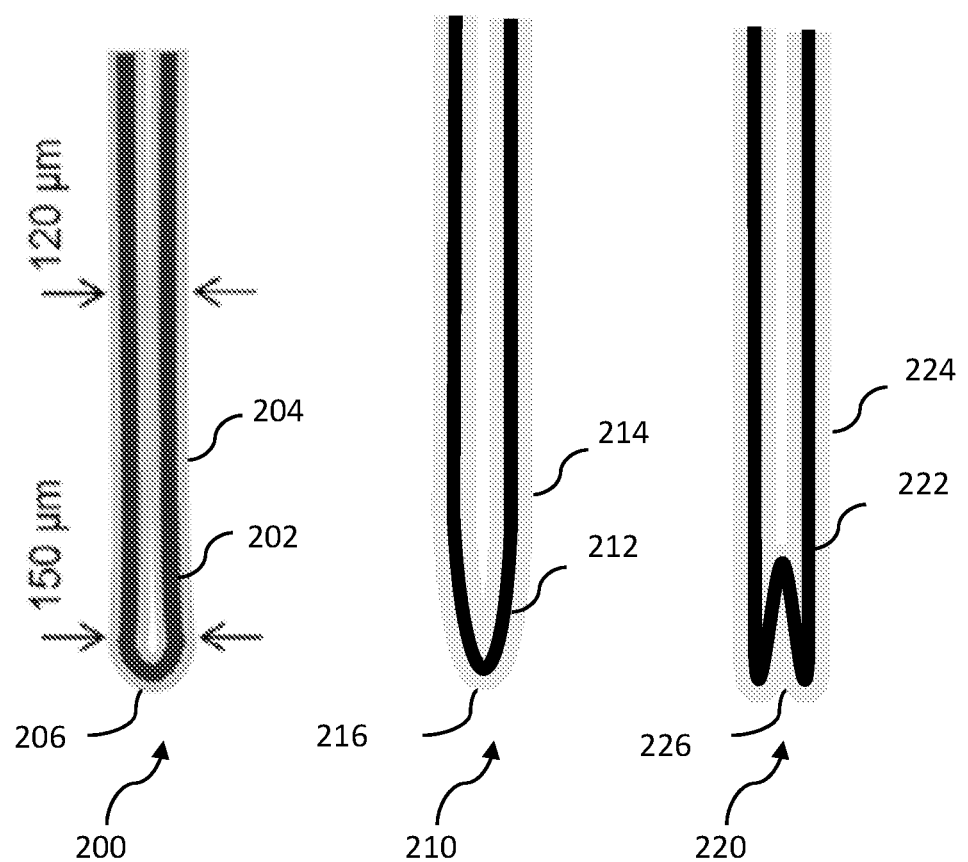
FIG. 2A depicts three exemplary bent micro-wires made by bending insulated micro-wires.

Exemplary stimulators that are small enough to be safely implanted, and yet capable of generating electric fields large enough for neuronal activation, may include insulated and bent micro-wires with, for example, one of the configurations shown in FIG. 2A. Micro-wire stimulator 200 includes a 50-μm diameter biocompatible metal wire (e.g., platinum, gold, platinum-Iridium, etc.) 202 surrounded by a 5-μm thick polyurethane/polyamide insulation 204. Micro-wires can be made with even smaller wires having, for example, 10 to 25 μm diameters. The width may be uniform along its length, or it could vary; for example, the width of the bent micro-wire stimulator 200 at its rounded tip portion 206, as shown, is 150 μm, tapering to 120 μm. It is noted that the separation between the arms (i.e., the substantially parallel portions extending from the rounded bend) can have a separation that ranges from 0 μm (such that the arms are touching, with the wires separated only by insulation) to around 250 μm.

Figure 2B:
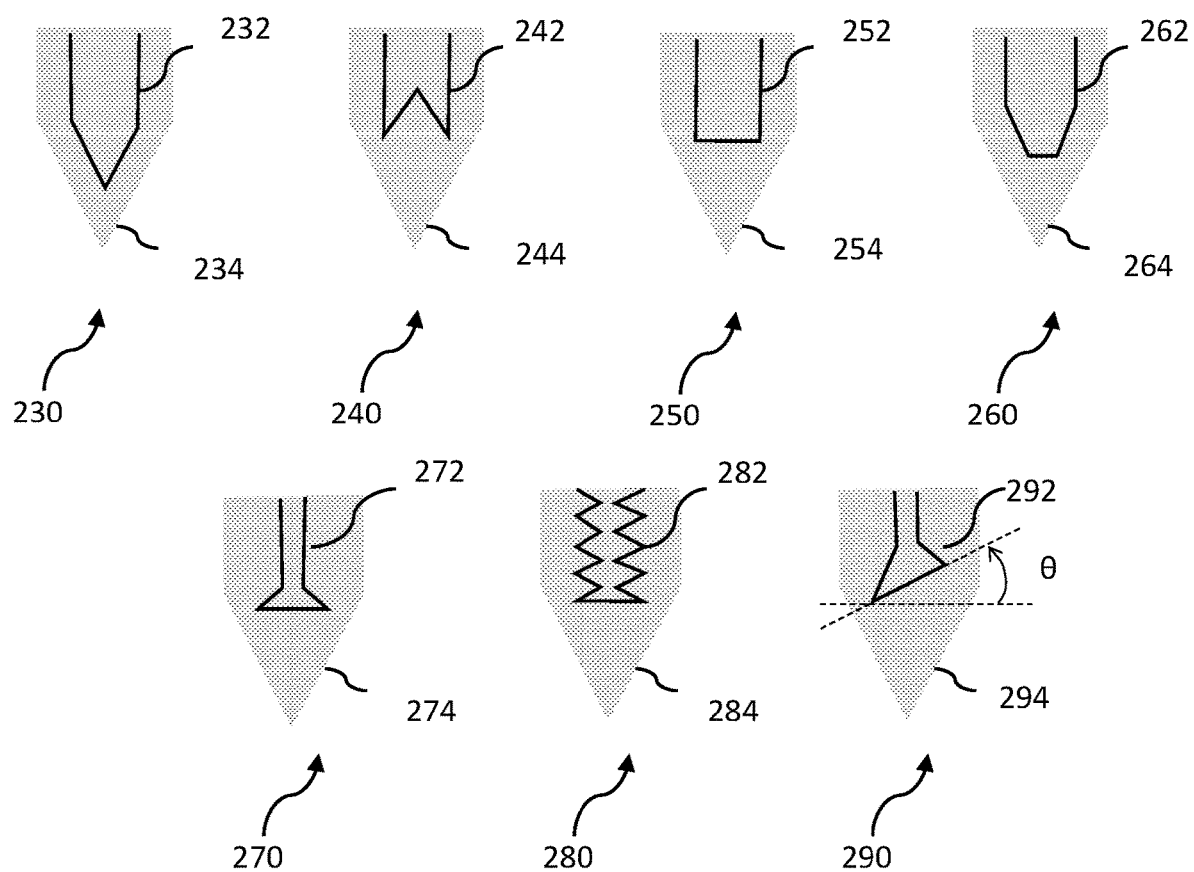
FIG. 2B depicts seven exemplary bent micro-wires formed on substrates by using micro-fabrication processes.

The exemplary stimulator 210 includes micro-wire 212 bent to form a more pointed tip portion 216, and stimulator 220 includes micro-wire 222 bent to form a "W" shape at tip portion 226. Micro-wires 212 and 222 include insulation 214, 224, respectively. Because electric fields for neuronal activation are magnetically induced and not generated through direct contact with a conductor, the stimulators may be insulated with a biologically inert material (e.g. polyimide, parylene-C, SU-8, polytetrafluoroethylene (PTFE), polycarbonate (PC), and Liquid Crystal Polymer (LCP)) that can help to reduce the reactions that can occur between the stimulator and biological tissue, extending the life of the stimulators and further minimizing the possibility of adverse effects in the tissue or other complications. Referring to FIG. 2B, alternative exemplary stimulators 230, 240, 250, 260, 270, 280, and 290 are shown. As will be further discussed below, conductive traces 232, 242, 252, 262, 272, 282, and 292 are situated on substrates 234, 244, 254, 264, 274, 284, and 294, respectively. It is noted that these are only several exemplary shapes among possible shapes, and many other designs may be alternatively or additionally used to achieve the desired selective stimulation depending on application and targeted cells and their processes (such as nerve fiber, axons, dendrites, etc.). Different shapes may be useful depending on, for example, the orientation of the targets, the portion(s) of the brain to be stimulated, the size or configuration of the desired array of micro-wires, etc.

Figures 3A, 3B, 3C:
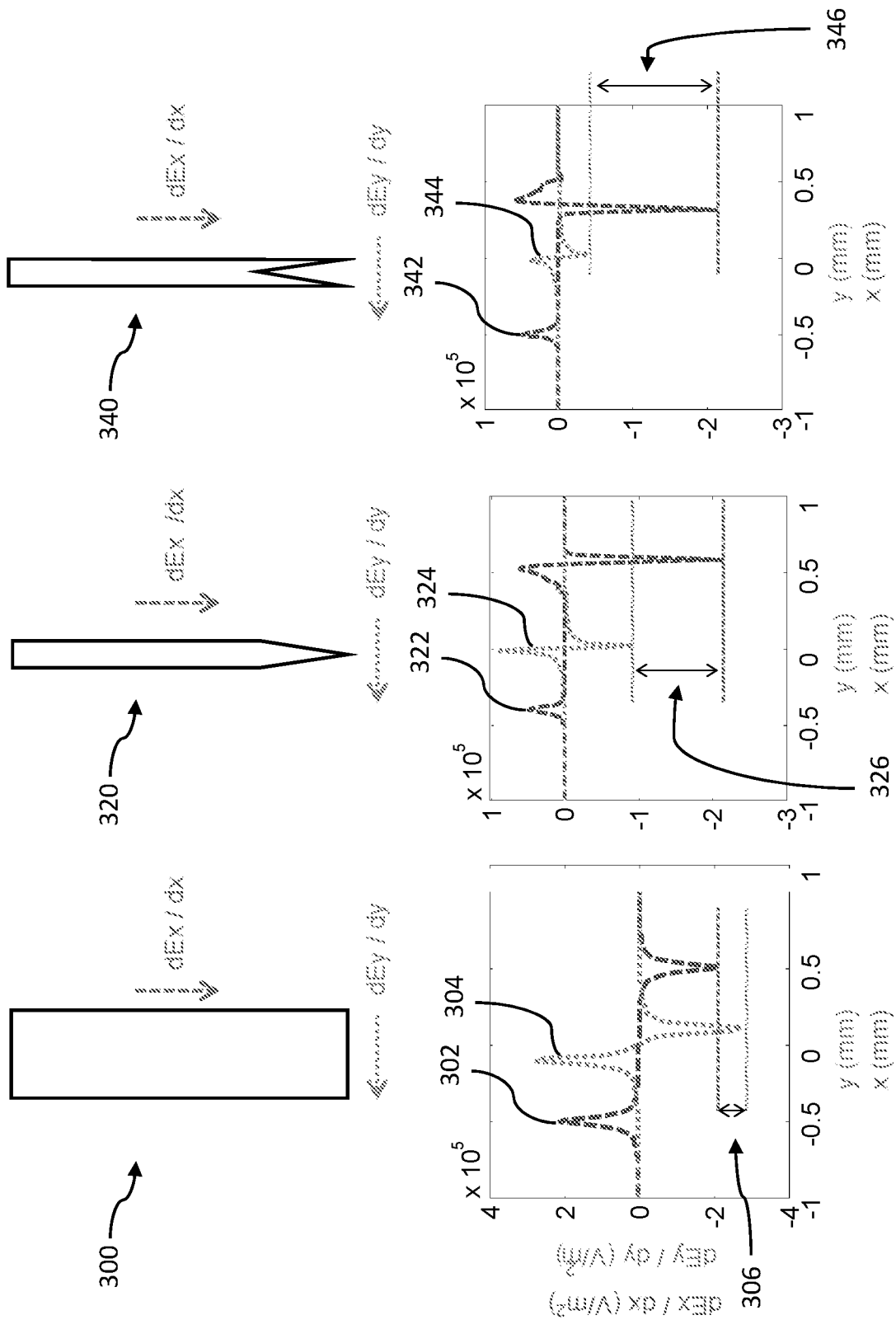
FIG. 3A depicts electric field gradient corresponding with activation (bottom) for an exemplary rectangular micro-wire loop design (top).
FIG. 3B depicts electric field gradient corresponding with activation (bottom) for an exemplary triangular micro-wire loop design (top).
FIG. 3C depicts electric field gradient corresponding with activation (bottom) for an exemplary W-shaped micro-wire loop design (top).

Computational modeling can be used to estimate the size of the magnetic field induced by exemplary configurations, as well as the resulting electric fields and their spatial gradients in 3 different orthogonal orientations. FIGS. 3A, 3B, and 3C show three stimulators 300, 320, and 340 (top) and their resulting field gradients (bottom) in the vertical (dashed lines 302, 322, 342, perpendicular to the cortical surface) and horizontal (dotted lines 304, 324, 344, parallel to the cortical surface) directions. The degree of asymmetry can be represented by the separation 306, 326, 346 between the valleys of gradients, with stimulator 340 exhibiting highly asymmetric electrical fields (i.e., the most asymmetry among the three stimulators 300, 320, 342). The large gradient of electric field in the vertical direction 342 for the "W" stimulator 340 (FIG. 3C), along with a weak gradient in the horizontal direction 344, makes this stimulator particularly well-suited for activating pyramidal neurons without simultaneously activating the passing axons from distal neurons.

As illustrated, changes to the shape of the bent wire can have a significant impact on the relative strengths of the horizontal and vertical gradients, and consequently, different stimulator designs can be used to create different activation profiles. For example, changes to the length, separation, sharpness as well as the number of the individual bends could be used to further modulate the asymmetry between the induced fields that arise along different orientations. In addition, other designs can be used to selectively target other types of cortical neurons (or other cells). For example, basket cells and chandelier cells (i.e., inhibitory interneurons) in the cortex have axons that extend horizontally; in cases where it is desirable to target such types of neurons, the metal wires can be designed to have a straight portion along the horizontal axis and a zigzag (repeating "W" shapes) 280 portion along the vertical axis. A "conical" shape with an elongated bottom (such as in 270) may also be used. As shown, the elongated bottom of 270 is linear, but need not be so; alternatively, the elongated bottom may be, for example, W-shaped, zig-zagged, helical, etc. (as can other linear segments of the exemplary micro-wires that are shown in the figures). In other configurations, the elongated bottom may be slanted at an angle Θ (such as in 290) with respect to a long axis of the micro-wire (or with respect to an axis orthogonal to the long axis of the micro-wire) so as to target or avoid neurons or interneurons at various different angles with respect to the micro-wire stimulator. Similarly, the elongated bottom of 290 also need not be linear but can have other shapes deemed suitable.

Figures 6A, 6B, 6C:
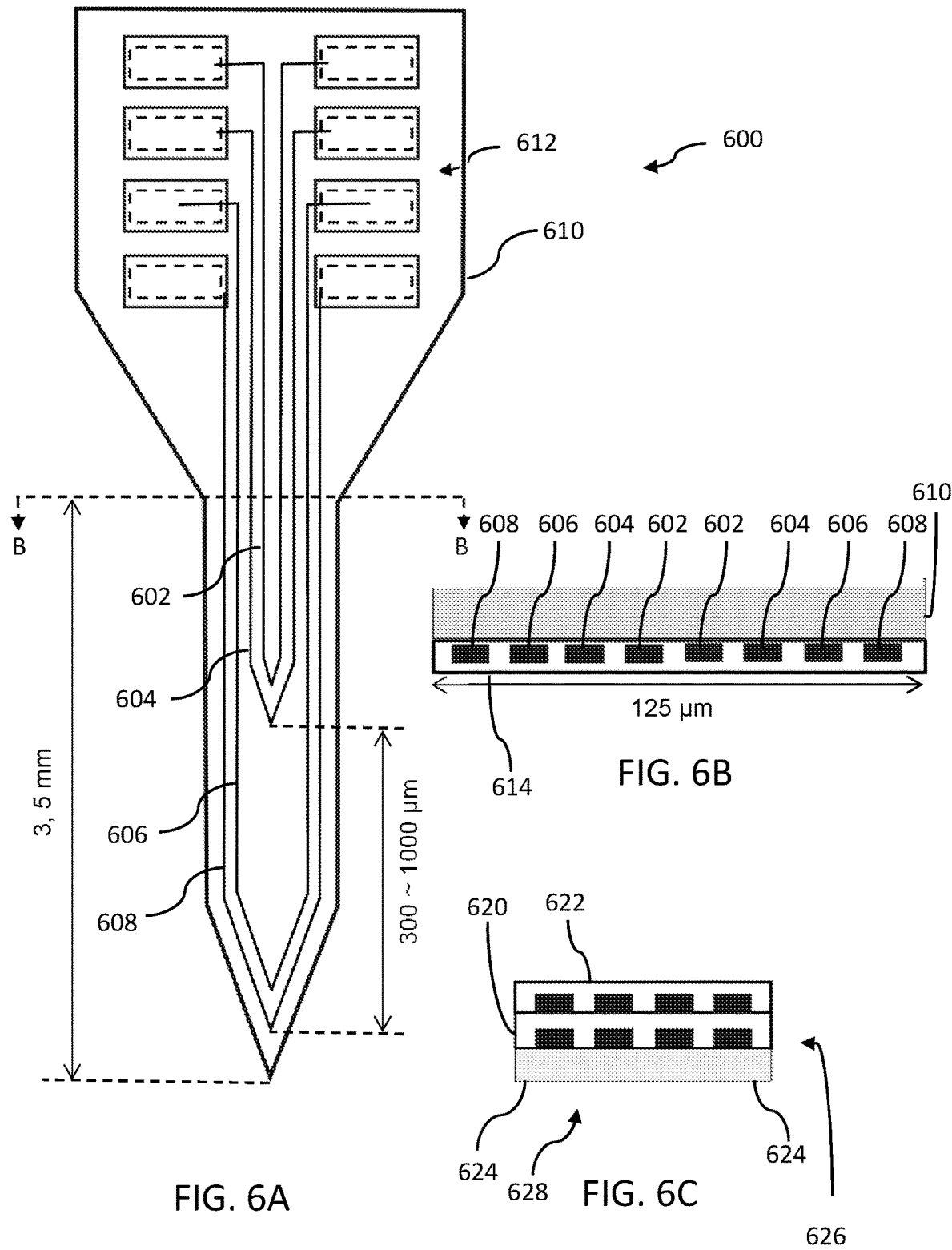
FIG. 6A depicts an exemplary multi-wire microprobe for stimulating cortex neurons, with micro-wires formed on a substrate.
FIG. 6B is a cross-sectional view of the microprobe of FIG. 6A along line B-B as indicated in FIG. 6A.
FIG. 6C is a cross-sectional view of alternative configurations in which multiple micro-wires are stacked into multiple layers.

It is further noted that the strongest part of the gradient typically corresponds to the parts of the wires with the sharpest bends. This allows specific cortical depths to be targeted using different shapes. Thus, for example, pyramidal neurons associated with Layer 2/3 can be driven independently of the pyramidal neurons associated with Layer 5. Additionally, as will be further discussed, different cortical layers can be targeted with, for example, penetrating probes of different lengths (FIG. 4), or, with single probes that contain multiple wire traces each "bending" at a different depth (FIG. 6A). Independent control of pyramidal neurons from each layer is particularly useful because the different types of neurons have distinct roles in the neural system. For example, L2/3 pyramidal neurons in visual cortex are thought to process conscious visual perception, whereas L5 neurons mediate eye movements.

Figure 13A:
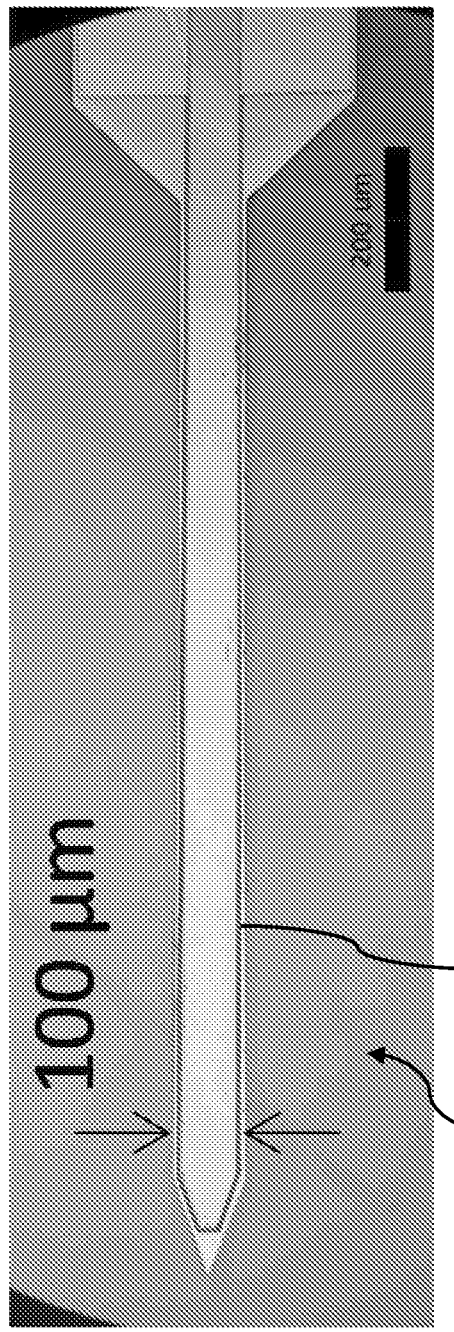
FIG. 13A depicts an exemplary microfabricated micro-wire.
Figure 13B:
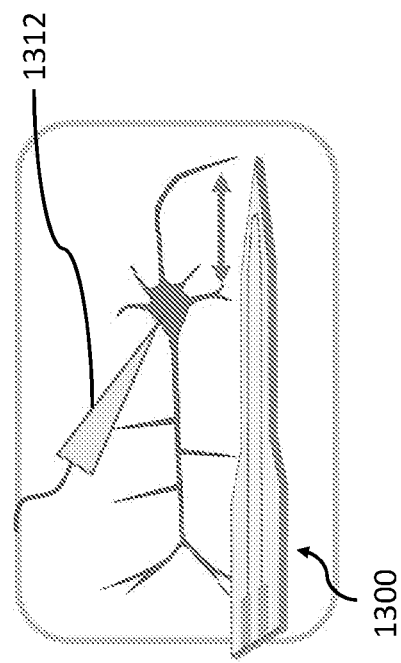
FIG. 13B is a schematic of an exemplary experimental setup in which a micro-wire assembly is positioned over the proximal axons in a parallel orientation.
Figure 13D:
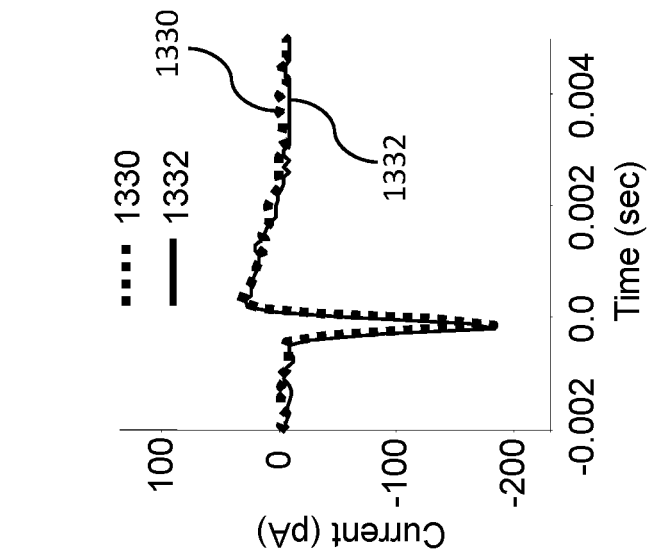
FIG. 13D indicates extracted neural responses (identical to spontaneous action potentials) to the proximal axonal stimulation shown in FIG. 13B without the application of the synaptic blockers.
Figure 13C:
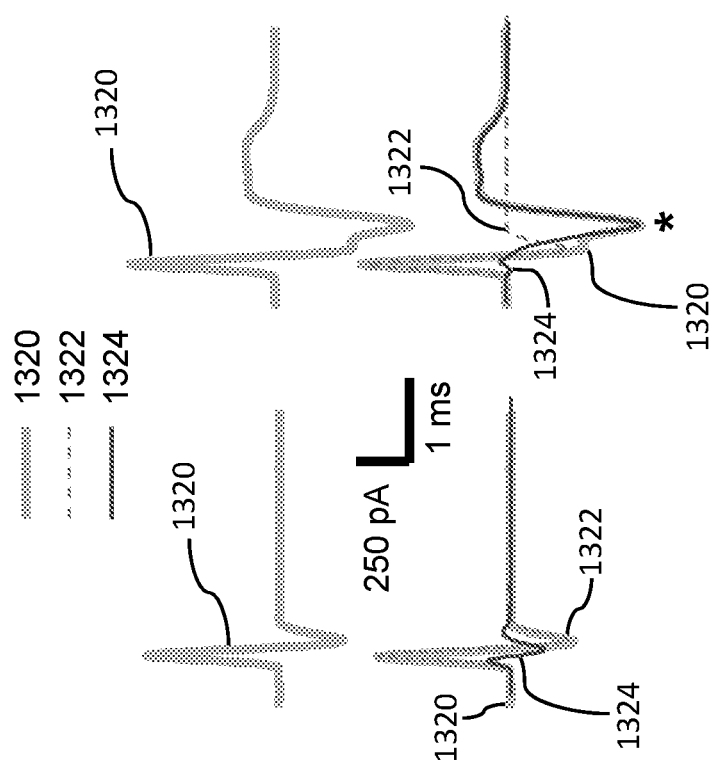
FIG. 13C depicts typical responses to the proximal axonal stimulation shown in FIG. 13B. Top left panel indicates responses to subthreshold stimulation, and top right panel indicates responses to suprathreshold stimulation. Bottom panels indicate the extracted neural responses by using application of synaptic blockers.

Fabricated micro-wires were first tested for their ability to activate cortical neurons during in vitro experiments using coronal brain slices from mice (FIG. 13A). In FIG. 13A, exemplary micro-wire stimulator 1300 includes copper trace 1302. A loose-seal cell-attached patch-clamp electrode 1312 was positioned on the soma of a targeted layer 5 (L5) PN within the whisker (motor) cortex (FIG. 13B) and used to record action potentials elicited by magnetic stimulation from the micro-wire 1300. Patch-clamp recordings have proven effective for allowing visualization of elicited action potentials in previous studies with electric stimulation because the amplifiers are not saturated by the stimulus; for example, the electrical artifact associated with the stimulus does not preclude observation of neuronal responses. The micro-wire was positioned close to the targeted cell with the tip centered over the proximal axon, the portion of the cell that is thought to have the highest sensitivity to stimulation (FIG. 13B). To ensure that observed responses arose from direct activation of the cell itself, that is, not secondary to activation of one or more presynaptic neurons, 10 μM 2,3-dihydroxy-6-nitro-7-sulfamoyl-benzo[f] quinoxaline (NBQX), 10 μM bicuculline, and 50 μM D-2-amino-S-phosphonopentanoic acid (D-APV) were added to the perfusion bath in some experiments to block synaptic input to the cell. Stimulation at relatively low amplitude levels produced an electrical artifact that consisted of a short-duration biphasic waveform that persisted for about 0.4 ms (FIG. 13C, upper left panel). Increasing the amplitude of stimulation slightly produced a similar artifact but continued into a more prolonged waveform (FIG. 13C, upper right panel). The addition of 1 μM tetrodotoxin (TTX) to the bath eliminated the prolonged part of the response (FIG. 13C, bottom right panel), suggesting that it was an action potential, and subtraction of the response in TTX from the corresponding control response revealed a waveform that was highly similar to those action potentials that arose spontaneously. Elicited action potentials could also be extracted from the raw recordings (without the use of TTX) by subtracting responses that contained the artifact only from those that contained an artifact plus an action potential (FIG. 13D); this process revealed a waveform that again had amplitude and kinetics that were nearly identical to those from a spontaneous action potential. This suggests that the direct subtraction method for identifying action potentials is comparably effective to the use of TTX. Together, these experiments indicate that magnetic stimulation from micro-wires can elicit action potentials through direct activation of L5 PNs. In FIG. 13C, line 1320 corresponds with a mix of artificial cerebrospinal fluid (aCSF), NBQX, bicuculline, and APV, line 1322 corresponds with TTX (artifact only), and 1324 with the subtracted. In FIG. 13D, 1330 corresponds with spontaneous action potential, and 1332 corresponds with evoked action potential.

Figure 14B:
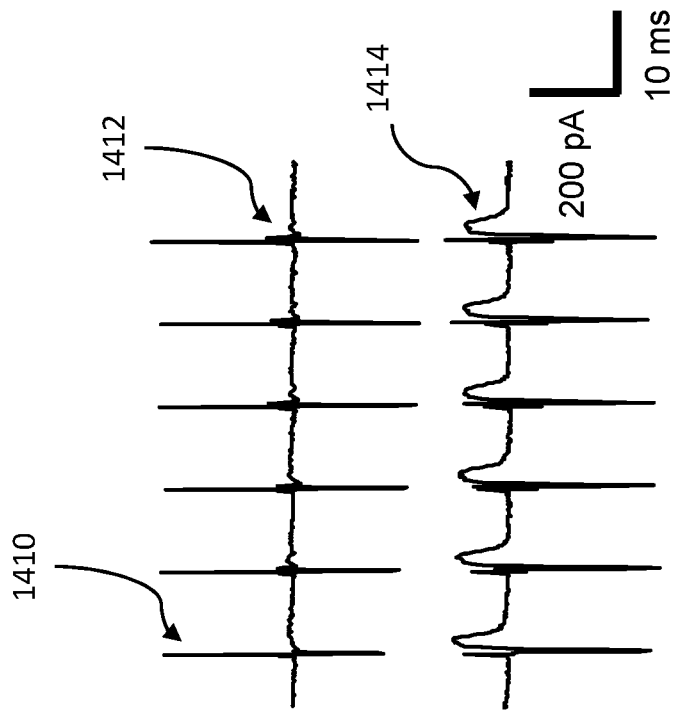
FIG. 14B depicts typical responses to the proximal axonal stimulation shown in FIG. 14A in a perpendicular orientation (top) and a parallel orientation (bottom).
Figure 14A:
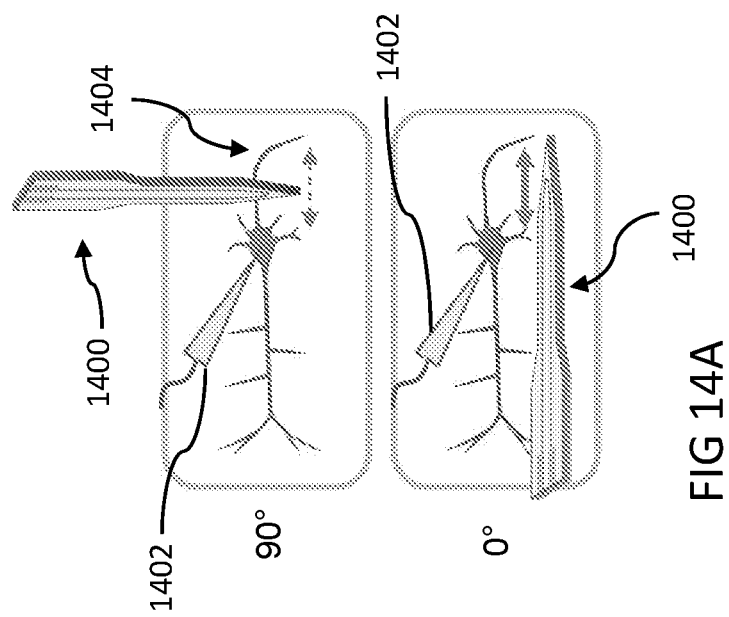
FIG. 14A is a schematic of an exemplary experimental setup in which a micro-wire assembly is positioned over the proximal axons in a perpendicular orientation (top) and a parallel orientation (bottom).
Figure 14C:
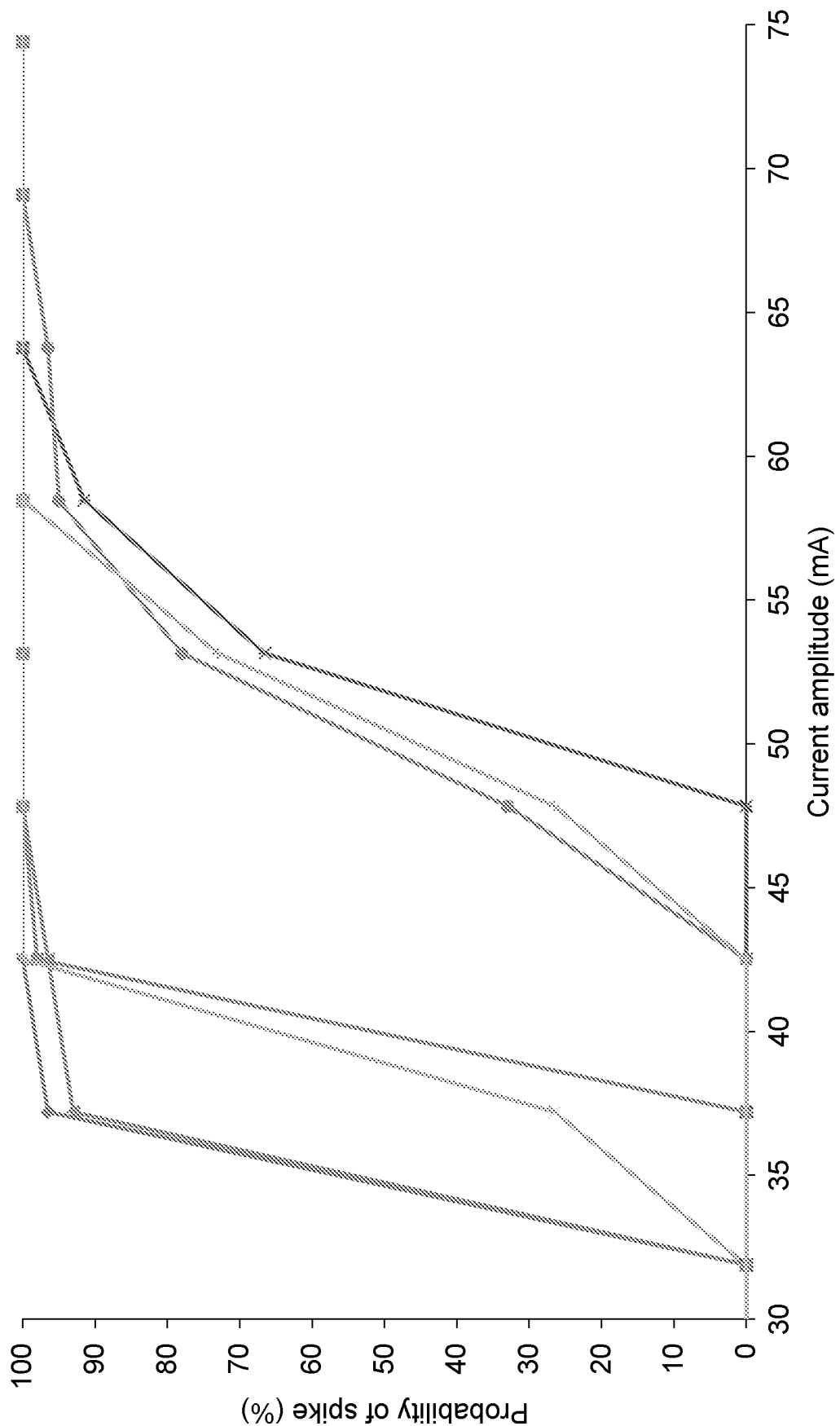
FIG. 14C depicts typical responsiveness (probability of activation) to the proximal axonal stimulation shown in FIG. 14A in a parallel orientation.

To explore the ability of the exemplary micro-wires to selectively target neurons, experiments were run in which the orientation of the micro-wire was varied relative to the orientation of the targeted PN (FIG. 14A). Initially, the plane of the micro-wire 1400 was held perpendicular to the surface of the slice (FIG. 14A, top), resulting in a weak electric field and gradient along the length of the neuron. In FIG. 14A, 1402 is a recording electrode, and 1404 is the proximal axon (AIS). As expected, this configuration was not effective (FIG. 14B, top), even for the strongest amplitude that could be delivered by our system. The micro-wire was then reoriented with its flat surface approximately parallel to the slice surface (FIG. 14A, bottom); this orientation is similar to that which would arise during insertion of the micro-wire into the intact cortex and resulted in a strong gradient along the length of the neuron that led to robust spiking; it is noted that the presence of the positive-going after-hyperpolarization that closely followed each stimulus provides a clear marker for the presence of an elicited action potential (FIG. 14B, bottom). In FIG. 14B, 1410 indicates stimulus artifacts, 1412 refers to no action potentials, and 1414 refers to action potentials. With direct activation, individual stimuli could each induce a single action potential at even the fastest rates tested (up to 100 Hz; n=11 of 11). Similar to electric stimulation, stronger levels of magnetic stimulation increased the likelihood that a given pulse would elicit a spike (n=7) and revealed thresholds of 44.21±7.31 mA (SD) for direct activation (FIG. 14C). The sensitivity to stimulation in these cells was not significantly affected by the addition of synaptic blockers to the perfusion bath (n=4). The ability to extract and visualize individual spikes also allowed the timing of individual spikes to be precisely determined and revealed onset latencies of 1.0 ms (FIG. 14D). As expected from spikes that are directly activated, latencies were not sensitive to the addition of synaptic blockers.

Referring to FIGS. 8A-8D, repositioning a micro-wire 800 such that its tip was over the apical dendrite 805 of the targeted neuron allowed the sensitivity of this portion of the neuron to be explored as well. Once again, orienting the plane of the micro-wire perpendicular to the slice surface (FIG. 8A) resulted in very weak electric fields along the neuron and did not produce spiking (FIG. 8B). However, alignment of the micro-wire parallel to the surface of the slice (FIG. 8C) produced robust spiking 815 (n=8; FIG. 8D). (Spikes/action potentials were measured using recording electrode 810 positioned at the soma 820 of the neuron.) The onset latencies of spikes elicited by stimulation over the apical dendrite were not well correlated to individual stimuli and were typically ms, suggesting that spikes were mediated through the activation of the surrounding neural network. The addition of pharmacological blockers of excitatory synaptic input to the perfusion bath [10 M CNQX (6-cyano-7-nitroquinoxalene-2,3-dione) and 50 M D-APV] eliminated these responses, thereby confirming their presynaptic origin. The thresholds for indirect activation were 46.50±11.78 mA (SD), and therefore both modes of activation had similar thresholds.

For direct activation, thresholds were generally lowest when the tip of the micro-wire was situated over the proximal axon at a distance of about 50 μm from the soma. For indirect activation, thresholds were generally lowest when the micro-wire was over the apical dendrite 805 at a distance of about 200 μm from the soma 820. It is noted that for the responses that arose through indirect activation (FIG. 8D), the electrical artifact arising from the stimulus was quite small. This is consistent with the spatially narrow extent of the induced electric fields versus the relatively large separation between the micro-wire and the recording electrode. Minimization of the stimulus artifact is a highly attractive feature, especially for efforts in which it is essential to record the response to artificial stimulation.

To test the effectiveness of certain implementations of micro-fabricated bent-wire stimulators for cortical activation, the stimulator shape depicted in FIG. 2B (rightmost, trapezoidal shape) was used in in vivo testing. The bent-wire stimulator design had a cross-sectional area of 50×100 μm, identical in size to that of an existing electrode (NeuroNexus) currently used for chronic implantation into cortex; consequently such a bent-wire stimulator may be safely implantable for chronic use. The micro-fabricated bent-wire stimulators were inserted into whisker (motor) cortex of anesthetized mice and led to reliable and robust whisker movements. Increasing the frequency of stimulation from 10 to 100 Hz reversed the direction of whisker movement from protraction to retraction. Taken together, the findings suggest that such stimulators can effectively drive neuronal circuits and further, their efficacy for driving neuronal circuits is at least comparable to that of electrodes.

The exemplary designs in FIGS. 3A, 3B, and 3C could be fabricated using a microfabrication process that involves, for example, a trace on a substrate. For example, each stimulator in FIGS. 3A, 3B, and 3C (rectangular 300, triangular 320, and W-shaped 340) could include a conductive metal (e.g., copper, platinum, gold, Titanium, platinum-Iridium, etc) on a substrate (e.g., silicon wafer, polyimide, parylene-C, SU-8, LCP, PTFE, PC, PET, ferrite, etc.) and insulated with a dielectric material (e.g., polyimide, parylene-C, SU-8, $SiO_2$/$Si_3N_4$, PC, PET, LCP, etc.). The overall dimension (cross-section) of exemplary microprobes could be 50×100 μm (or smaller). For example, sizes of 25×25 μm, comparable to existing commercial intra-cortical microprobes (NeuroNexus neural probe), could be used.

Figure 6D:
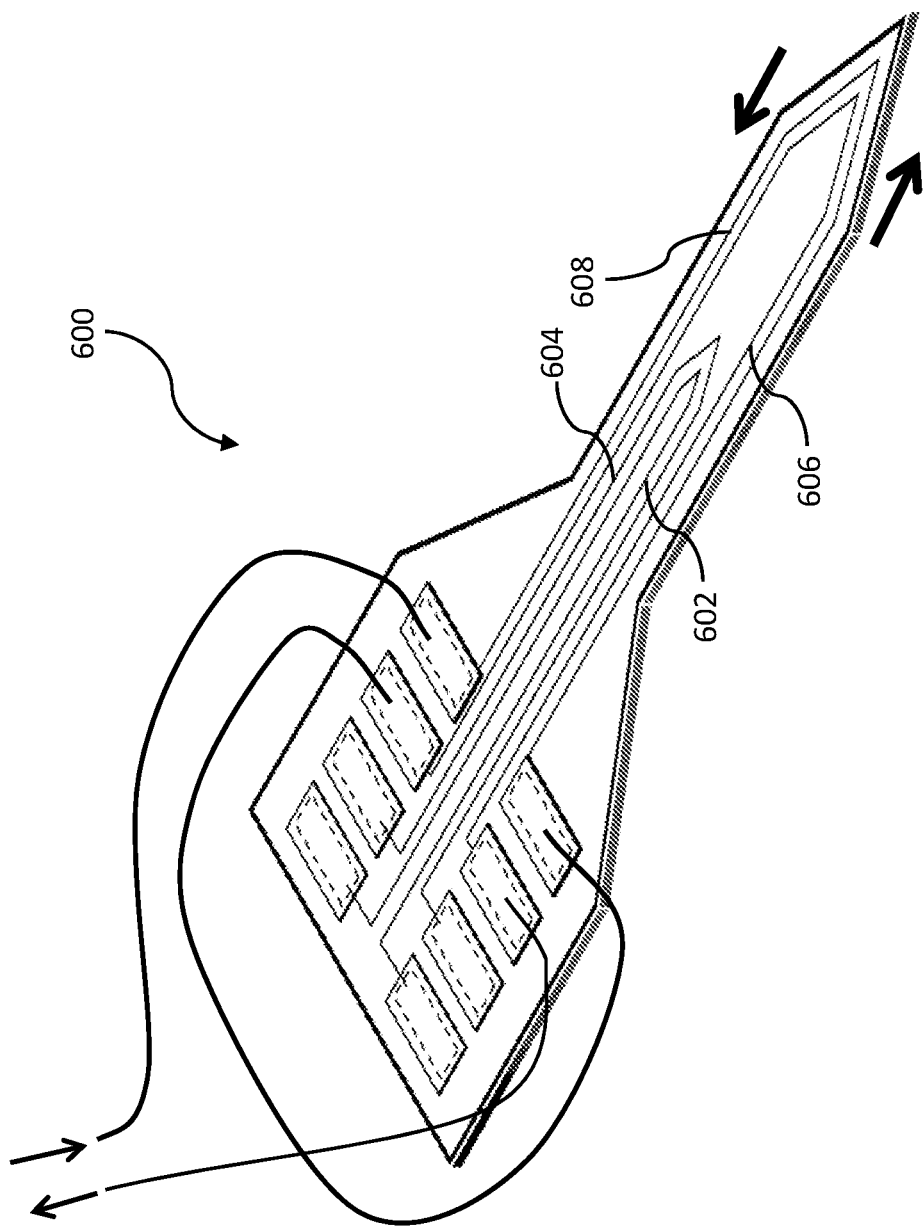
FIG. 6D is a perspective view of the exemplary microprobe of FIG. 6A, showing potential wiring of contact pads so as to link/connect micro-wires, forming loops with electrical paths extending through multiple (two or more) micro-wires in each loop.

Referring to the exemplary stimulator probe 600 in FIGS. 6A and 6D, micro-wires 602, 604, 606, 608 may be placed on substrate 610. Contact pads 612 (or other couplers) may be used to connect with the ends (or other portions) of the micro-wires to form "loops" extending from, for example, a first pad connected to a first end of a micro-wire, to a second pad connected to a second end of the same micro-wire, or to another micro-wire. Electrical input may be provided to the micro-wires via contact pads 612. Exemplary contact pads are metallic (including, for example, copper or other suitable metals and alloys) with a contact pad window that may be, for example, 300×200 μm~3000×2000 μm. In alternative configurations, multiple micro-wires could be connected so as to increase the number of micro-wires through which current "loops" (with respect to the path traveled by the current being supplied), thereby enhancing the strength of stimulation. For example, micro-wires 606, 608 can be paired ("linked") by being connected (via corresponding contact pads) as illustrated in FIG. 6D to form a two-micro-wire loop. The lengths of micro-wires 602, 604, 606, 608 can also be adjusted to target different layers in the cortex. As shown, exemplary micro-wire pair 602, 604 may extend, for example, 300 to 1000 μm further than micro-wire pair 606, 608. It is noted that induced current is in an opposite direction to that of the electric current in the micro-wire.

In the cross-sectional view of FIG. 6B, it can be seen that micro-wires 602, 604, 606, and 608 are situated on substrate 610. Exemplary micro-wires may have widths, for example, ranging from about 5 to 10 μm and thicknesses ("heights" with respect to the substrate 610), for example, ranging from about 3 to 10 μm. The micro-wires may be metallic lines that include, for example, copper and/or other suitable metals and alloys. The micro-wires are covered by an insulation coating that may have, for example, a thickness ("height" with respect to the substrate 610) ranging from about 3 to 10 μm. The substrate 610 may have a thickness/height, for example, ranging from about 15 to 30 μm, and a shank width, for example, of about 125 μm, depending on the particular application.

In alternative versions, stimulator 600 may include "layers" of micro-wires "stacked" on top of each other. For example, referring to the cross-sectional view of an exemplary stimulator in FIG. 6C, a first insulation coating layer 620 may be situated (sandwiched) between a second insulation coating layer 622 and substrate 624. In the version shown, four micro-wires are embedded in each of the two coating layers 620, 622, although fewer or more wires may be provided. The micro-wires may have similar dimensions as those depicted in FIGS. 6A and 6B. Because the number (and thickness) of each layer can vary, the thickness 626 of the probe/stimulator varies. For example, in exemplary versions, the thickness may range from about 10 to 200 μm. The shank width 628 is also variable, and can range from, for example, 10 to 200 μm. Dimensions are adjustable to suit particular implementations.

Figures 7A, 7B:
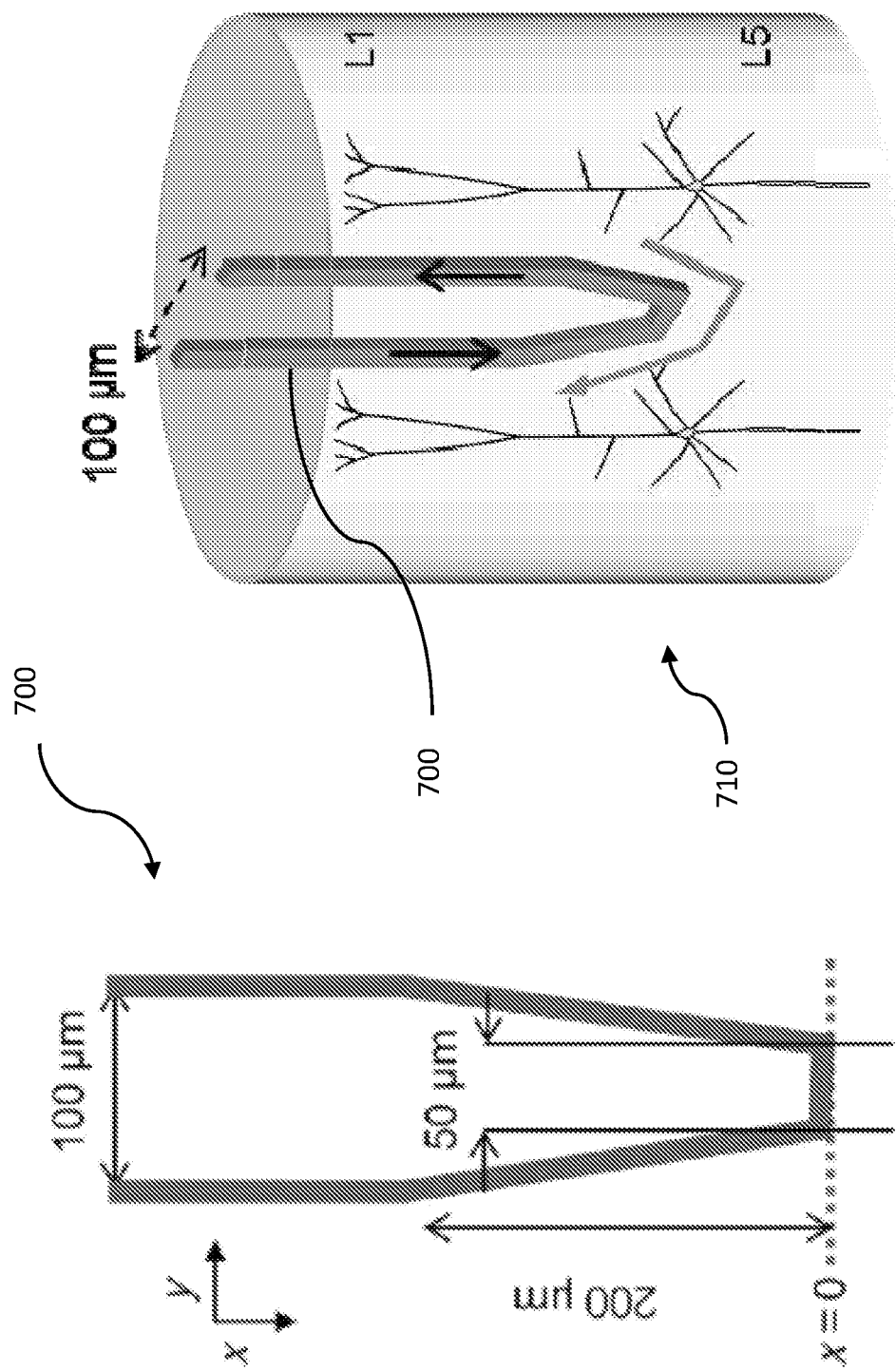
FIG. 7A depicts an exemplary micro-wire with a trapezoidal tip portion with four bends.
FIG. 7B depicts the exemplary micro-wire of FIG. 7A inserted in a cortical column.

To verify activation of cortical neurons, the bent-wire stimulator 700 of FIG. 7A was microfabricated for use in physiological experiments (further discussed below). Stimulator 700 is a trapezoid-shaped loop that is 100 μm wide, with a width that tapers down to 50 μm at the tip over a (lengthwise) span of 200 μm. The bent micro-wire included a copper trace (10 μm wide×2 μm thick) on a silicon substrate that had a cross-sectional area of 50 μm×100 μm and a length of 2000 μm; it was similar in size to FIG. 13A. The micro-wire assembly had a DC resistance of about 15 ohms and was insulated with 300 nm of $SiO_2$ to prevent the leakage of electric current into the tissue. A second, similarly sized micro-wire 200 (FIG. 2A) was also constructed by carefully bending a 50-μm-diameter copper wire. Although this second micro-wire did not have as sharp a bend as the microfabricated micro-wire 700 of FIG. 7A, the thicker cross-sectional area of the wire allowed stronger currents. Five-micrometer polyurethane/polyamide insulation prevented the leakage of electrical current from micro-wire 200 into the bath or tissue. Its resistance was about 13 ohms. FIG. 7B depicts the insertion of micro-wire 700 into cortical column 710.

Figure 9B:
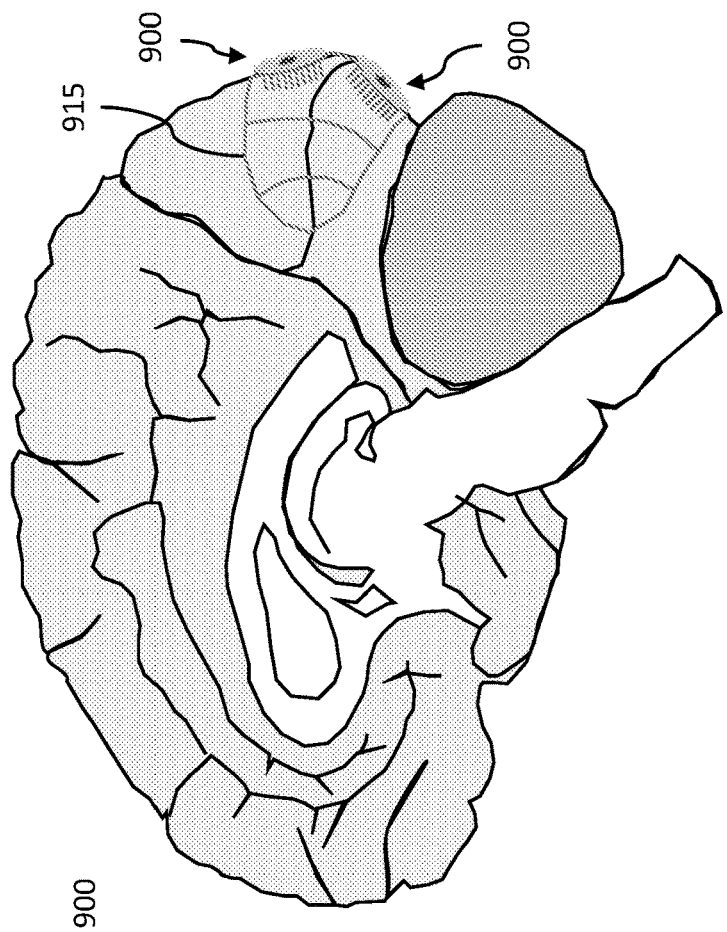
FIG. 9B depicts a brain with a pair of exemplary micro-wire implants positioned in the visual cortex.
Figure 9C:
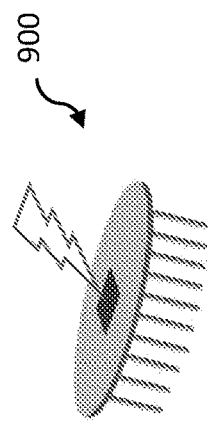
FIG. 9C is the exemplary micro-wire implant depicted in FIGS. 9A and 9B.
Figure 9A:
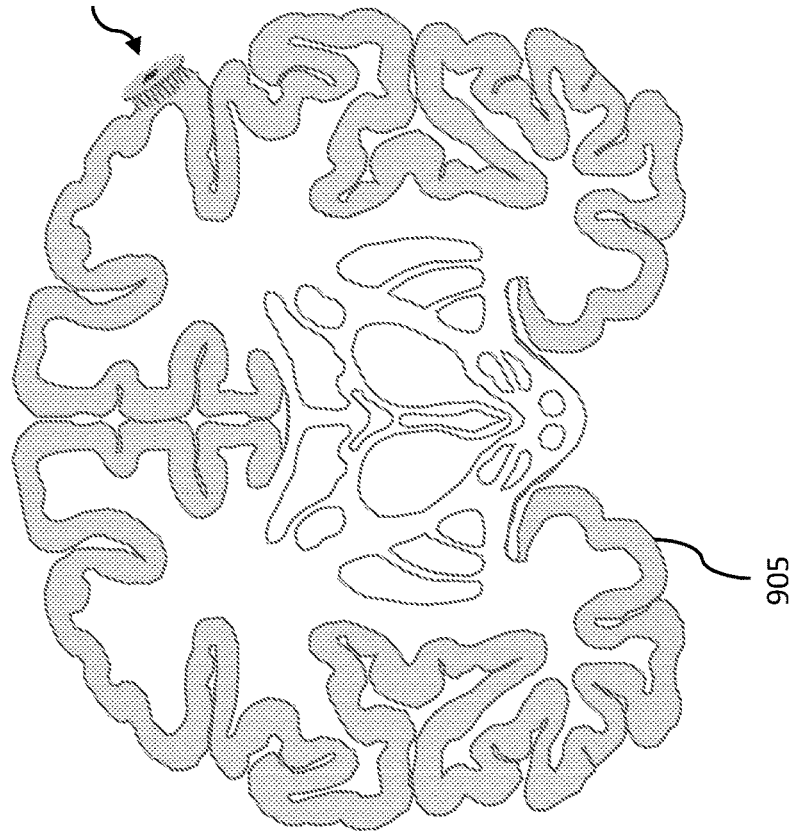
FIG. 9A depicts a brain with an exemplary micro-wire implant positioned in the cortex.

Referring to FIGS. 9A-9C, an exemplary multi-wire microprobe array 900 is implanted into the cortex 905 (gray matter) of a brain. The wires may be assembled in the array 900 as depicted in the exemplary probe array of FIG. 5. In FIG. 5, multiple micro-wires 502 are assembled into a single array 500. Such an array 500 would allow simultaneous stimulation of, for example, multiple regions of cortex, and would therefore be well-suited for building spatially complex visual patterns or delivering multiple somatosensory percepts simultaneously. Electronics that generate stimulating current pulses may be incorporated, as can telemetry links for receiving data and power wirelessly. The 3D multi-wire array 900 (FIG. 9A) could be used for a wide range of cortical prostheses that require high-resolution stimulation, for example, a motor cortex implant (FIG. 9A)

or a visual cortex 915 implant (FIG. 9B). Exemplary microwire-based arrays may also be insertable into somatosensory, inferotemporal or other regions of cortex as well.

Referring to FIG. 10, an exemplary process of magnetically stimulating cells may begin by positioning the stimulator to be used (1000). This may involve implantation of the stimulator in the cortex (such as the motor cortex or visual cortex). With the stimulator in place, a current may be applied to one or more micro-wires in the stimulator (1005), so as to activate one or more neurons (1010) or other cells.

Referring to FIG. 11, a system 1100 for magnetic stimulation may include one or more micro-wires 1105 as discussed above. A pulse generator 1110 may provide stimulating current pulses (a wide array of stimulus waveforms can be used, e.g. full or half-sinusoids, trapezoids, Gaussian, etc.). Generator 1110 provides the electrical input to generate the magnetic field that will induce an electric field in the brain (or other targets). A telemetry unit 1115 supports wireless communication/transfer between the stimulator and an external source of data and/or power. Data and power may be communicated or transmitted via, for example, radio frequency (RF) communication protocols, near-field communication (NFC), inductive interaction, etc. The memory 1120 and processor 1125 may control the telemetry unit 1115 to send and receive, for example, control or status information. A power source 1130, such as a battery, may be used to power the system 1100. Alternatively or additionally, operating power may be provided by transcutaneous inductive power generation, with or without a battery.

It is noted that a "bend" in the exemplary micro-wires discussed above refers to a change in direction in the micro-wire. The bend may be sharp (forming a corner where two segments intersects at an angle), but need not be so. As disclosed above, the change in direction may a rounded intersection of segments meeting where the direction is changed. It is also noted that the approach discussed above may be adapted for activation of any electrically active cells, including neurons outside the cortex, including peripheral axons as well as muscle cells. It is moreover noted that use of the term "micro" in "micro-wire" is not intended to limit the range of sizes (widths, diameters, lengths) that could be used in exemplary wires.

Further, although conventional coil-based inductors could potentially generate magnetic fields that achieve selective neuronal activation, the cross-sectional profile of even the smallest such inductors (500 µm in diameter and 1 mm long) are nearly 100 times that of commonly used electrode implants, and cannot be safely implanted into the cortex. Also, existing micro-coil inductors require thresholds of 717 mA for activation, whereas the thresholds for in vitro activation with exemplary versions of the micro-wire discussed above were 44.21 mA (about 16 times smaller). The lower threshold levels that were observed here likely arose because the smaller size of the micro-wires not only generated stronger fields but also allowed for closer proximity to targeted neurons. It is noted that the magnitude of the gradients from the exemplary micro-fabricated bent-wire stimulators are comparable in magnitude to the gradients that would result using larger (and impractical) conventional coil inductors, and can be expected to be similarly effective in activating neural cells.

Figures 12A, 12B:
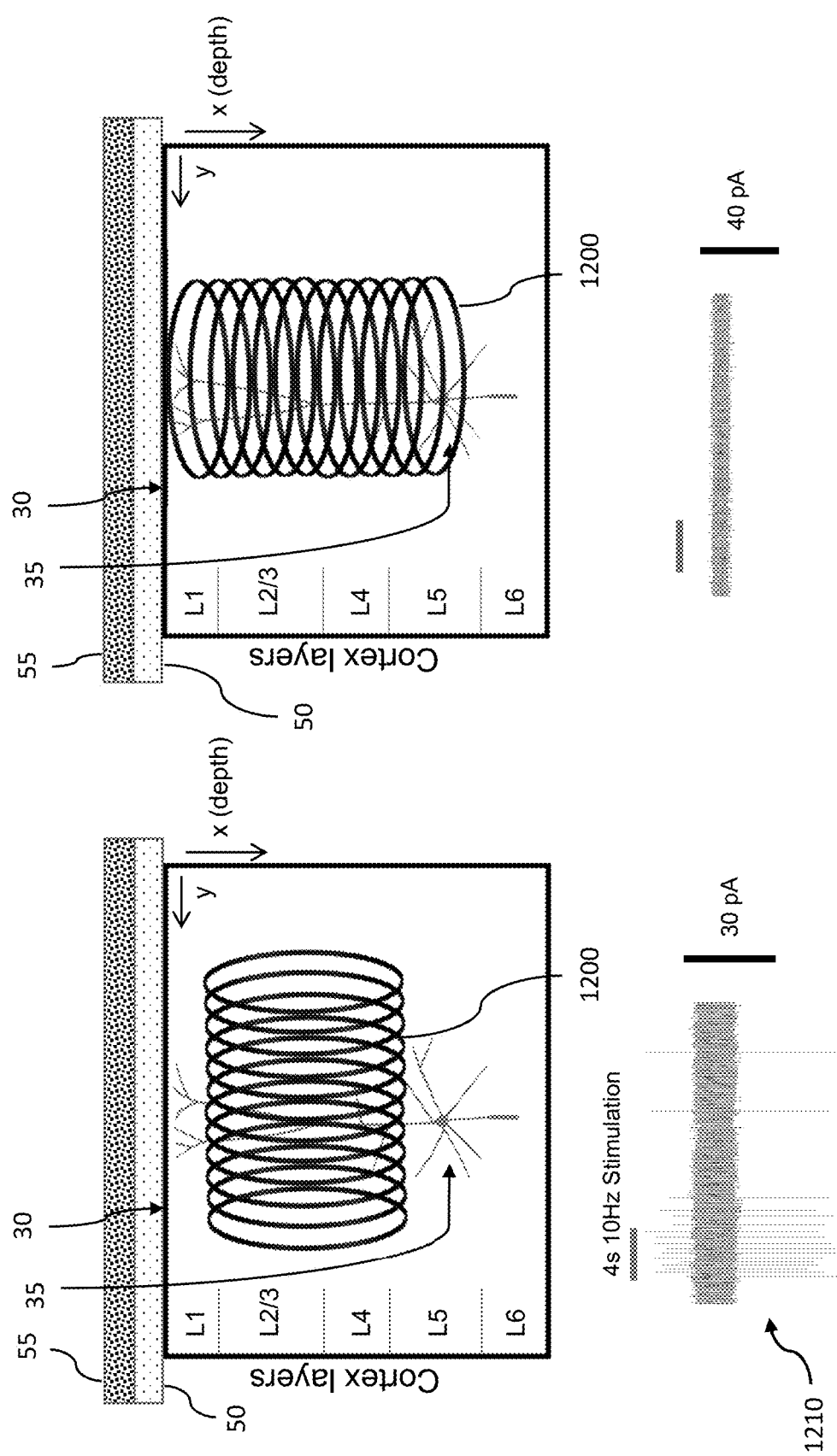
FIG. 12A depicts orientation of a conventional coil-based inductor (top) to achieve a response (action potentials, bottom) in L5 pyramidal neurons (PNs) of cortex.
FIG. 12B depicts an orientation of the conventional coil-based inductor (top) of FIG. 12A, and the lack of responses (bottom) in L5 PNs.

Referring to FIGS. 12A and 12B, another limitation of conventional coil-based inductors can be seen. In FIG. 12A (top), conventional inductor coil 1200 has its long axis parallel with the brain surface 30. This orientation may produce electric fields strong enough to elicit action potentials 1210 seen in the bottom of FIG. 12A. Referring to FIG. 12B, if inductor 1200 is oriented with its long axis perpendicular with brain surface 30, the very weak electric fields produced along the neuron does not elicit the spiking (bottom). It would be significantly more difficulty to insert inductor 1200 in the orientation shown at the top of FIG. 12A, with its entire length penetrating the brain surface 30, than to insert inductor 1200 in the orientation shown at the top of FIG. 12B, with its width penetrating the brain surface 30. For this additional reason, coil-based inductors are not practical for implantation and cannot safely be used for stimulating the same targets targeted using conventional electrodes.

Modeling of bent-wire stimulators: To calculate or model the spatial gradient of induced electric fields (E-fields) arising from the flow of current through differently-shaped exemplary micro-wires, some or all of the following relationships may be applicable.

From Faraday's Laws, the E-field, $\vec{E}$, is related to the time varying magnetic field by:

$$\nabla \times \vec{E} = -\frac{\partial \vec{B}}{\partial t} \quad (1)$$

Because the magnetic field, $\vec{B}$, can be obtained by taking the curl of the magnetic vector potential, $\vec{A}$, (i.e. $\vec{B} = \nabla \times \vec{A}$) the equation for E-field can be expressed as:

$$\vec{E} = -\frac{\partial \vec{A}}{\partial t} -, \nabla V \quad (2)$$

Under the assumptions that there is no charge on the micro-wire and the current distribution in the micro-wire is uniform (that is, quasi-static condition), $\nabla V$ is equal to 0 and Eqn. 2 becomes:

$$\vec{E} = -\frac{\partial \vec{A}}{\partial t} \quad (3)$$

The magnetic vector potential is calculated from the micro-wire geometry as follows:

$$\vec{A} = \frac{\mu_0 N i}{4\pi} \cdot \oint \frac{dl}{R} \quad (4)$$

where $\mu_0$ is the permeability constant, N is the number of turns, i is the electric current through the micro-wire, R is the vector between the micro-wire segment and the target segment at which the E-field is calculated, and dl is the small segment of the micro-wire.

If the principal axis of the pyramidal neurons (PNs) within each cortical column is approximately parallel to the x-axis, the E-field along the cortical column can be calculated by numerically integrating along the length of the micro-wire loop.

$$\partial \vec{E}_x = -\frac{\mu_0 N \left(\frac{di}{dt}\right)}{4\pi} \cdot \oint \frac{1}{R} dl_x \quad (5)$$

where the x-dimension corresponds to the long axis of the PN.

Integrating the $\partial \vec{E}_x$ with respect to the x component of the line gives the following equation for $\vec{E}_x$.

$$\vec{E}_x = -\frac{\mu_0 N \left(\frac{di}{dt}\right)}{4\pi} \cdot \ln\left[x - x_0 \sqrt{(x-x_0)^2 + (y-y_0)^2 + (z-z_0)^2}\right]_{x_1}^{x_2} \quad (6)$$

In Eqn. 6, the micro-wire element lies at $(x_0, y_0, z_0)$ and the E-field is calculated at $(x, y, z)$. The $x_1$ and the $x_2$ represent the positions of the corners of the rectangular micro-wire in the x-axis. The spatial gradient, $$\frac{\partial \vec{E}_x}{\partial x},$$

is calculated by taking the derivative of the analytical solution for $\vec{E}_x$ from Eqn. 6. The input current to the micro-wire, i, was a half period of 3 kHz sinusoidal waveform with an amplitude of 1 mA.

Fabrication and testing of exemplary bent-wire stimulators: An exemplary fabrication process is based on silicon processing techniques. First, a 50 µm thick 4-inch silicon wafer may be bonded to a handling wafer with an adhesive. Subsequently, a 100-200 nm SiO2 layer may be deposited using plasma-enhanced chemical vapor deposition (PECVD). Then a 2 µm thick copper layer may be sputtered using electron beam (e-beam) assisted physical vapor deposition (PVD) with a 10 nm thin titanium layer to improve adhesion. Next, a photoresist, used as mask for the next etching step, may be spin-coated and baked. The photoresist can be patterned by exposure to UV light through a phase-shifting photomask. After that, the copper may be wet-etched using a solution of Transene Copper Etch 49-1. The photoresist can be stripped off in acetone and then 300 nm insulating SiO2 may be deposited on top using PECVD. The area of the electrical contact pads may be shadowed to help ensure it is free of the top insulation. Following this step, a photoresist, used as the mask in the silicon etch, may be spin-coated and patterned. The 50 µm thick silicon substrate may be etched through using deep reactive ion etching (DRIE). The resulting bent-wire structures are then released from the handling wafer in acetone and dried. A bent-wire structure may also be made using, for example, an ultra-fine copper wire (50 µm bare diameter (45-AWG), Polyurethane base coat, Polyamide overcoat, 60 µm with insulation, Essex, Fort Wayne, Ind., USA).

In other implementations, the fabricated bent-wires were assembled with copper wire leads (34-AWG, polyurethane inner coat and nylon over coat) (Belden, Richmond, Ind., USA). The electrical contacts of micro-wires were connected to the copper wire leads using a silver conductive epoxy (CircuitWorks Conductive Epoxy, ITW Chemtronics, Kennesaw, Ga., USA). Assembled micro-wires were mounted on a custom-made plastic holder with an instant adhesive and the distal ends of the copper wire leads were attached to the signal and ground leads of a BNC connector. The custom-made assemblies were secured to the micromanipulator of a stereotaxic frame (Model 900, David Kopf instruments, Tujunga, Calif., USA) for accurate positioning over mouse cortex.

Each micro-wire assembly was tested both before and after each experiment to ensure that there was no leakage of electrical current from the micro-wire into the mouse cortex. Micro-wires were submerged in physiological solution (0.9% NaCl) and the impedance between one of the micro-wire terminals and an electrode immersed in the physiological solution was measured before and after each in vivo animal experiment. Impedances above 200 MΩ were considered indicative of adequate insulation. The high impedance ensured that direct electrical currents did not contribute to any of the elicited neural activity underlying observed mouse behaviors.

Micro-magnetic stimulation drive: In certain implementations, the output of a function generator (AFG3021B, Tektronix Inc., Beaverton, Oreg.) was connected to a 1,000 W audio amplifier (PB717X, Pyramid Inc., Brooklyn, N.Y.) with a gain of 5.6 V/V and a bandwidth of 70 kHz. The audio amplifier was powered by a battery (LC-R1233P, Panasonic Corp., Newark, N.J.). The output of the amplifier was monitored with an oscilloscope (TDS2014C, Tektronix Inc., Beaverton, Oreg.). Stimulation pulses may consist of a single full period 3 kHz sinusoid waveform. The amplitude of sinusoids from the function generator ranged from 0-200 mV. The output of the amplifier for sinusoids was 0-1.12 V. Single burst stimulation consisting of 5 pulses or 10 pulses was delivered at 10 Hz and 100 Hz, respectively. Repetitive stimulation at 1 pulse per second was delivered for a total of 10 seconds. Other repetitive stimulations consisted of 3 pulses per second at 10, 50, or 100 Hz for a total duration of 5 seconds.

The present disclosure has described one or more preferred embodiments, and it should be appreciated that many equivalents, alternatives, variations, and modifications, aside from those expressly stated, are possible and within the scope of the invention.

The invention claimed is:

1. A method for stimulating cells and/or their processes in a subject, the method comprising:
   positioning a stimulator proximal to the cells to be stimulated, the stimulator including:
      a first end, and a second end opposite the first end, the first and second ends defining a length of the stimulator;
      a first surface, and a second surface opposite the first surface; and
      a micro-wire, the micro-wire extending towards the second end along a first portion of the length of the stimulator, extending along a portion of a width of the stimulator, and extending back towards the first end along a second portion of the length of the stimulator, wherein the micro-wire is part of a probe that includes a set of micro-wires, and wherein two micro-wires are connected such that current travels through a loop formed by the two connected micro-wires; and
   providing an electrical input to the micro-wire to provide an electrical current that travels through the loop of the micro-wire that generates a magnetic field that induces an electric field in the subject;
   wherein the cells are selectively activated based on the orientation of the micro-wire relative to the cells, and wherein the loop of the micro-wire is planar.

2. The method of claim 1, wherein the micro-wire is insulated with a biologically inert dielectric.

3. The method of claim 1, wherein the cells include at least one of:
   neurons;

neurons, axons, and/or dendrites in the cortex;
neurons, axons, and/or dendrites in the deep brain;
neurons, axons, and/or dendrites in the basal ganglia;
neurons, axons, and/or dendrites in the spinal cord; or
neurons, axons, and/or dendrites of peripheral nerves.

4. The method of claim 3, wherein the cells include neurons, axons, and/or dendrites in the cortex, and
wherein the micro-wire is positioned in the cortex of the subject.

5. The method of claim 4, wherein the micro-wire is one micro-wire in an array of micro-wires, and wherein the array of micro-wires is positioned in the visual cortex of the subject to generate visual percepts.

6. The method of claim 4, wherein the micro-wire is positioned in at least one of:
a motor cortex of the subject;
a somatosensory cortex of the subject; or
a motor cortex and a somatosensory cortex of the subject.

7. The method of claim 4, wherein at least one of the following occurs:
neurons aligned orthogonal to a surface of the cortex are activated;
neurons aligned parallel to a surface of the cortex are activated;
neurons aligned parallel to a surface of the cortex are not activated; or
neurons aligned orthogonal to a surface of the cortex are not activated.

8. The method of claim 1, wherein the micro-wire includes a tip portion that is at least one of triangular, trapezoidal, W-shaped, partly zig-zagged, or partly conical shaped.

9. The method of claim 1, wherein the micro-wire includes a tip portion terminating in an elongated portion that is perpendicular to a long axis of the micro-wire.

10. The method of claim 1, wherein the micro-wire includes a tip portion terminating in a substantially elongated portion that is angled at an angle $\theta$ with respect to a long axis of the micro-wire.

11. The method of claim 1, wherein the micro-wire includes at least one of a tip portion that is rounded or a conductor formed on a substrate.

12. A method for stimulating cells and/or their processes in a subject, the method comprising:
positioning a stimulator proximal to the cells to be stimulated, the stimulator including:
a first end, and a second end opposite the first end, the first and second ends defining a length of the stimulator;
a first surface, and a second surface opposite the first surface; and
a micro-wire, the micro-wire extending towards the second end along a first portion of the length of the stimulator, extending along a portion of a width of the stimulator, and extending back towards the first end along a second portion of the length of the stimulator, wherein the micro-wire is part of a probe that includes a set of micro-wires; and
providing an electrical input to the micro-wire to provide an electrical current that travels through the loop of the micro-wire that generates a magnetic field that induces an electric field in the subject;
wherein the cells are selectively activated based on the orientation of the micro-wire relative to the cells,
wherein the loop of the micro-wire is planar, and wherein the probe includes at least two micro-wires with different lengths.

13. The method of claim 12, wherein the cells are neurons in the cortex of the brain of the subject, and wherein the method further comprises activating one or more neurons in a shallower layer of the cortex using a relatively short micro-wire, and activating one or more neurons in a deeper layer of the cortex using a relatively longer micro-wire.

14. The method of claim 12, wherein stimulation is independently applied at multiple depths.

15. A system for stimulating a cortex of a subject, the system comprising:
a stimulator including:
a substrate having a first end, and an opposite second end, the first and second ends defining a length of the substrate;
a first loop of a first micro-wire, the first loop of the first micro-wire coupled to the substrate, the first micro-wire extending towards the second end along a first portion of the length of the substrate, extending along a second portion of a width of the substrate, and extending back towards the first end along a third portion of the length of the substrate; and
a second loop of a second micro-wire, the second micro-wire coupled to the substrate, the second micro-wire extending towards the second end along a fourth portion of the length of the stimulator, extending along a fifth portion of the width of the substrate, and extending back towards the first end along a sixth portion of the length of the stimulator, the fifth portion of the second micro-wire being separated from the second portion of the first micro-wire by a distance along the length of the substrate; and
a generator coupled to the first and second micro-wires to provide an electrical input thereto,
wherein the first and second micro-wires are configured to receive the electrical input that generates a first magnetic field for the first micro-wire, and a second magnetic field for the second micro-wire, the first magnetic field extending along the entirety of the first and third portions of the first micro-wire, and the second magnetic field extending along the entirety of the fourth and sixth portions of the second micro-wire, the first and second magnetic fields being configured to selectively excite neurons based on the orientation of the first and second micro-wires relative to the neurons.

16. The system of claim 15, wherein vertically oriented pyramidal neurons (PNs) are activated over horizontally-oriented passing axons.

17. The system of claim 15, further including a telemetry unit for receiving data or power.

18. The system of claim 15, wherein the system forms at least one of a visual cortex implant and a motor cortex implant.

19. A device for stimulating a cortex of a subject, the device comprising:
a first end, and a second end opposite the first end, the first and second ends defining a length of the stimulator;
a first surface, and a second surface opposite the first surface; and
an insulated micro-wire, the micro-wire extending towards the second end along a first portion of the length of the stimulator, extending along a portion of a width of the stimulator, and extending back towards the first end along a second portion of the length of the stimulator, wherein the insulated micro-wire is part of a probe that includes a set of micro-wires, and wherein two micro-wires are connected such that current travels through a loop formed by the two connected micro-wires, and the micro-wire being configured to receive an electrical input that generates a magnetic field to induce a spatially asymmetrical electric field, and the loop of the insulated micro-wire being planar.

20. The device of claim 19, wherein the micro-wire extending along a portion of a width of the simulator defines a tip portion of the micro-wire, and wherein the tip portion has at least one of a concave or a convex shape.

\* \* \* \* \*

UNITED STATES PATENT AND TRADEMARK OFFICE
CERTIFICATE OF CORRECTION

PATENT NO.         : 11,007,372 B2                                           Page 1 of 1
APPLICATION NO.    : 16/086584
DATED              : May 18, 2021
INVENTOR(S)        : Seungwoo Lee et al.

It is certified that error appears in the above-identified patent and that said Letters Patent is hereby corrected as shown below:

In the Specification

Column 7, Line 42, "D-2-amino-S-" should be --D-2-amino-5- --.

Column 8, Line 56, "typically ms" should be --typically $\geq$ 3 ms--.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*